United States Patent
Ostrovsky et al.

(10) Patent No.: US 10,413,161 B2
(45) Date of Patent: Sep. 17, 2019

(54) ENDOSCOPE TIP ATTACHMENT DEVICE

(71) Applicant: HOYA Corporation, Tokyo (JP)

(72) Inventors: Issac Ostrovsky, Wellesley, MA (US); Azadeh Khanicheh, Somerville, MA (US); Hrishikesh Vishvas Deo, Brooklyn, NY (US); Robb Morse Gavalis, Westborough, MA (US)

(73) Assignee: Hoya Corporation, Tokyo (JP)

( * ) Notice: Subject to any disclaimer, the term of this patent is extended or adjusted under 35 U.S.C. 154(b) by 297 days.

(21) Appl. No.: 15/200,046

(22) Filed: Jul. 1, 2016

(65) Prior Publication Data
US 2017/0112365 A1 Apr. 27, 2017

Related U.S. Application Data

(60) Provisional application No. 62/245,711, filed on Oct. 23, 2015.

(51) Int. Cl.
*A61B 1/00* (2006.01)
*A61B 1/31* (2006.01)
(Continued)

(52) U.S. Cl.
CPC .......... *A61B 1/0008* (2013.01); *A61B 1/0014* (2013.01); *A61B 1/00085* (2013.01);
(Continued)

(58) Field of Classification Search
CPC .............. A61B 1/0008; A61B 1/00082; A61B 1/00085; A61B 1/00089; A61B 1/00101; A61B 1/00131; A61B 1/00133; A61B 1/00135; A61B 1/0014; A61B 1/00147; A61B 1/00154; A61B 1/00156; A61B 1/01; A61B 1/273; A61B 1/2733;
(Continued)

(56) References Cited

U.S. PATENT DOCUMENTS 5,556,376 A * 9/1996 Yoon ................ A61B 17/00234
604/11
5,653,690 A 8/1997 Booth et al.
(Continued)

FOREIGN PATENT DOCUMENTS

JP 2003-339631 A 12/2003
JP 2003339631 A * 12/2003 ......... A61B 1/00089
(Continued)

OTHER PUBLICATIONS

PCT Notification of Transmittal of the International Search Report and the Written Opinion of the International Searching Authority issued in International Application No. PCT/IB2016/001056, dated Oct. 24, 2016.

*Primary Examiner* — Ryan N Henderson
(74) *Attorney, Agent, or Firm* — Finnegan, Henderson, Farabow, Garrett & Dunner, LLP

(57) ABSTRACT

Embodiments of the disclosure include an endoscope tip assembly for use on an endoscope, during procedures. The endoscope tip assembly may include a base, configured to receive an endoscope tip configured to not disengage from the endoscope tip during a procedure. The endoscope tip assembly may also include a plurality of struts, connected by a webbing, that may fold flat during insertion, and may assume a balloon-like shape during withdrawal.

11 Claims, 27 Drawing Sheets

(51) Int. Cl.
 *A61B 1/32* (2006.01)
 *A61M 25/04* (2006.01)
(52) U.S. Cl.
 CPC ...... *A61B 1/00089* (2013.01); *A61B 1/00101* (2013.01); *A61B 1/00137* (2013.01); *A61B 1/31* (2013.01); *A61B 1/32* (2013.01); *A61M 25/04* (2013.01)
(58) Field of Classification Search
 CPC ........ A61B 1/2736; A61B 1/31; A61M 25/04; A61M 29/00; A61M 3/0291
 USPC ......... 600/114–116, 127, 129; 604/104–109; 606/191–200
 See application file for complete search history.

(56) References Cited

U.S. PATENT DOCUMENTS

| | | |
|---|---|---|
| 2006/0161046 A1 | 7/2006 | Ouchi |
| 2008/0058590 A1* | 3/2008 | Saadat ............... A61B 1/00085 600/109 |
| 2013/0090527 A1 | 4/2013 | Axon |
| 2013/0096550 A1 | 4/2013 | Hill |
| 2015/0148606 A1 | 5/2015 | Rottenberg et al. |

FOREIGN PATENT DOCUMENTS

| | | |
|---|---|---|
| WO | WO 2011/148172 A2 | 12/2011 |
| WO | WO 2014/123563 A1 | 8/2014 |

* cited by examiner

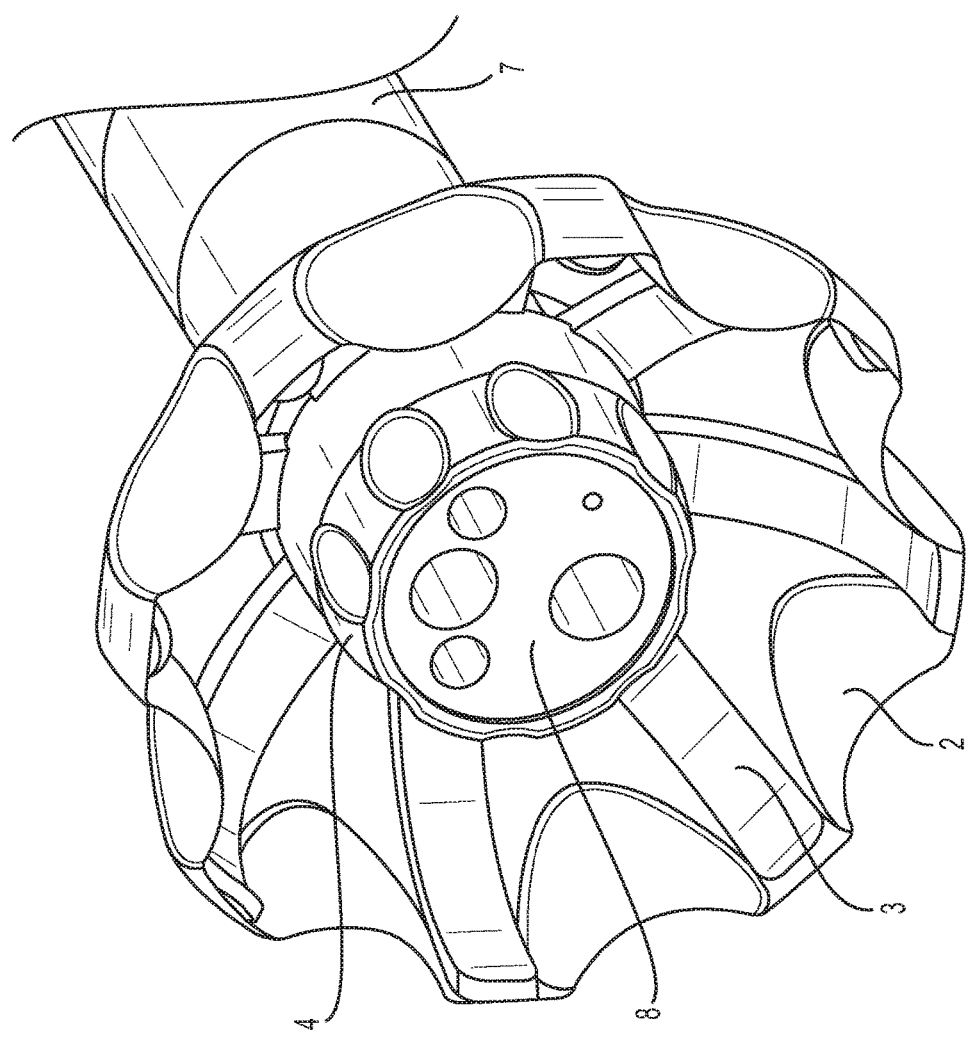

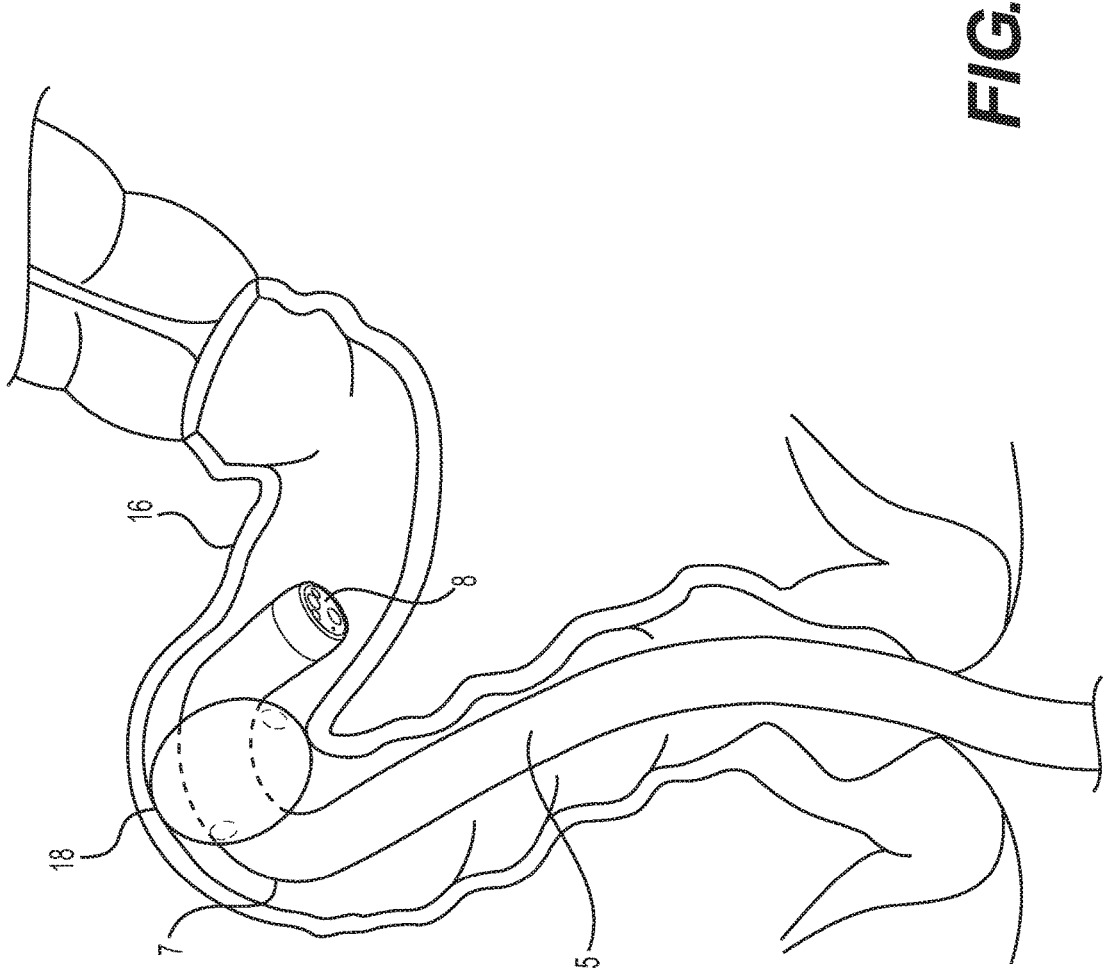

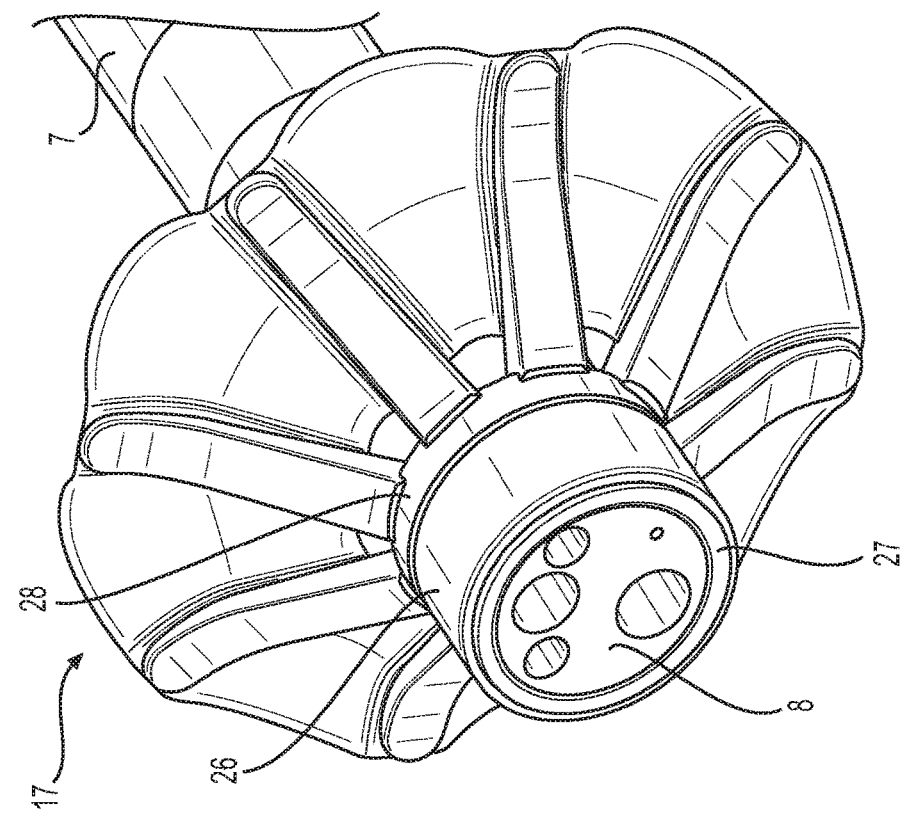
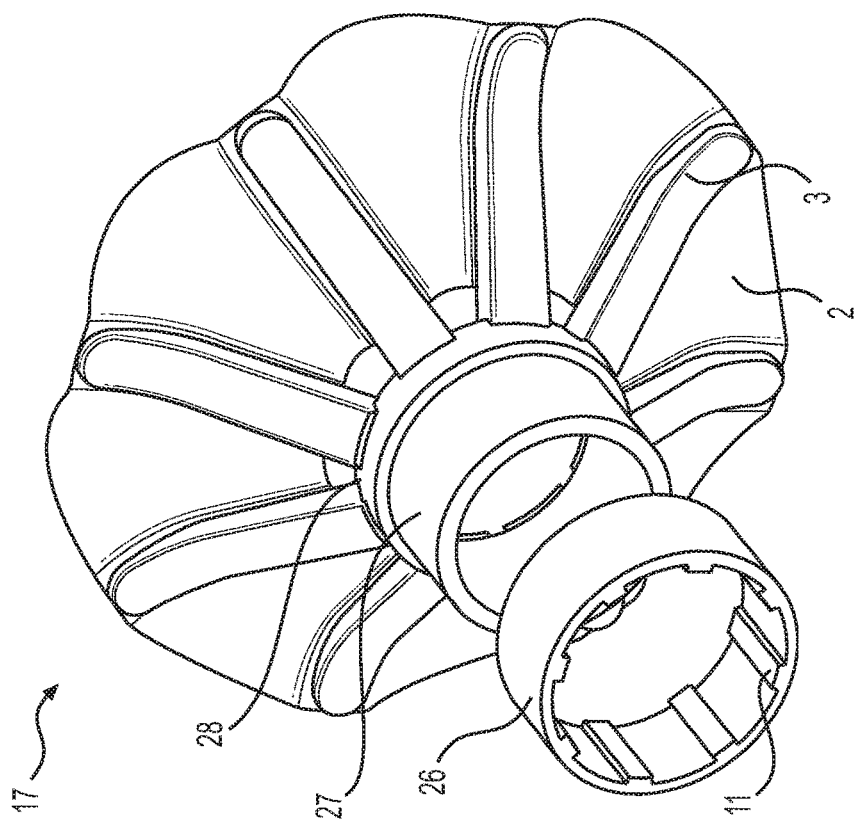
*FIG. 19B*
*FIG. 19A*

ENDOSCOPE TIP ATTACHMENT DEVICE

CROSS-REFERENCE TO RELATED APPLICATIONS

This application claims the benefit of U.S. Provisional Application No. 62/245,711, filed on Oct. 23, 2015.

TECHNICAL FIELD

Embodiments of the present disclosure relate to an endoscope accessory and, more particularly, to an endoscope tip assembly for supporting the distal tip of an endoscope and/or for improving field of view of an endoscope during use.

BACKGROUND INFORMATION

In endoscopic procedures, endoscopes are inserted through an orifice or incision and through the body lumen. The endoscope may be guided through internal body lumens, e.g., the gastrointestinal tract, to a region of interest, such as the stomach, cecum, duodenum, small intestine, large intestine, or esophagus. The instruments are provided with a fiber-optic, charge-couple device (CCD), or a CMOS camera, which enable images to be transmitted along the flexible endoscopes and reproduced on a display external to the body of the patient. Accordingly, it is possible to view the internal surfaces of body lumens during these procedures. For example, a gastroscope may be used to view the internal surfaces of the esophagus, stomach, or duodenum.

Endoscopic procedures may be used to provide visual diagnosis (e.g., of an ulceration or polyp), treatment, biopsy, and/or removal of tissue. While colonoscopic and enteroscopic examinations may be effective techniques to assess the state of health of an internal body region, they may cause complications and, in some instances, may fail to allow a clinician to accurately visualize a region of interest. For example, a clinician may not be able to complete the procedure, may fail to detect a polyp, lesion, or other structure, or may cause injury to the body lumen in which the endoscope is inserted, e.g., via the application of traumatic force, which may result in inflammation, burns, bleeding, scarring, perforation, or other injury.

Endoscopic procedures may be time consuming for patients and medical personnel alike, depending upon how difficult it is to advance a scope through the body lumen or to view the surrounding region. Increased procedure times require a patient to be sedated for longer periods, may increase patient discomfort, and thus may increase recovery time. Additionally, there is an in-hospital recovery period, which may last several hours while the anesthesia wears off, and, during that time, clinical observation is needed. Increased procedure time further cuts down on the number of procedures that a given team of clinicians can perform in one day and limits the use of an operating room.

Anatomical and technological limitations may also contribute to the difficulties of these procedures. First, the anatomy of a body lumen, e.g., the colon, may be tortious, and the lining may be uneven. For example, the colon is arranged into a series of folds. As the tip of the endoscope passes along the lumen of the colon, these folds may hamper the clinician's ability to visualize the entire surface of the mucosa and, in particular, to detect pre-malignant and malignant lesions and polyps located along these folds. For example, during endoscope withdrawal, lesions located on the distal faces of these folds may not be visualized.

Second, the tip position of the endoscope may be difficult to maintain once a lesion or polyp is detected and/or during a therapeutic, diagnostic, or biopsy procedure. Due to gravity, the endoscope tip may not stay centered within the colon and may instead fall against the wall of the colon. As a colonoscope is inserted or withdrawn, the tip may slide and drop inconsistently along the colon as it moves over the folds. This movement and/or the effect of gravity may cause the clinician to become disoriented, lose visualization, or lose positioning. If tip position is lost, time must be taken to again relocate the region of interest.

Additionally, the tortious nature of the gastrointestinal tract may make it difficult for a clinician to navigate the endoscope to the region of interest. The turns of the bowel, folded surface of the colon, and effects of gravity may cause the endoscope to bump and press on the body lumen as the endoscope is advanced or withdrawn. This may lead to stretching of the bowel, perforation, bleeding, trauma to the mucosa, inflammation, or other injury. As a result, the patient may experience pain, the patient's recovery time may increase, procedure time may increase, or the procedure may even need to be aborted prematurely.

A number of products have attempted to address the challenges associated with endoscopic procedures. For example, active balloon endoscopes and balloon attachments have been developed. The balloons are inflated once inserted into the colon to assist with withdrawal and visualization. However, these devices may be complex to manufacture and use due to the need for inflation and deflation mechanisms and the delicateness of the expanding portions. Additionally, active balloons that form a permanent part of an endoscope make scope-reprocessing (e.g., high level cleaning and disinfection) more challenging.

Other distal endoscope attachments that have rows of protrusions have been developed to aid in opening up colonic folds. However, the protrusions of those devices typically provide very similar stiffness and resistance to force in the direction of insertion and the direction of withdrawal. However, when inserting an endoscope, it is desirable to have reduced resistance on the distal tip. Since insertion involves two motions, linear advance and torqueing, the resistance to both of those motions should be low. Upon withdrawal, a device should engage with the colon to open the folds. This means that protrusions should be compliant and have low flexing and torqueing stiffness upon insertion, and should be configured to interact and engage with the colon and have relatively higher flexing stiffness upon withdrawal. If the protrusions are stiff upon insertion, this may cause increased insertion resistance, which then might cause the scope to loop and stretch the colon walls. This might produce mucosal trauma as the endoscope is inserted or withdrawn. Additionally, the force applied by the tips of the protrusions to discrete surface areas of the wall of the body lumen may increase mucosal trauma or cause perforation. On the other hand, if the protrusions are not stiff on withdrawal, they may not be capable to open the colonic folds and may not help with visualization of the regions adjacent the folds, as intended.

Accordingly, an improved endoscope attachment device is needed that is more compliant upon insertion and has a higher resistance to force upon withdrawal. Such a device may be capable of safely and effectively reducing the time taken for a clinician to perform an endoscopic procedure and for increasing the effectiveness of the procedure.

The device of the present disclosure aims to overcome the limitations of the prior art by facilitating one or more of the following: low resistance in an insertion direction; more effective opening of folds on withdrawal, steadying and/or centering the endoscope tip's position during a medical procedure; reducing the potential for mucosal trauma; and/or providing better physical and/or visual access around colonic folds.

SUMMARY OF THE EMBODIMENTS

Embodiments of the present disclosure relate to an endoscope tip assembly. Various embodiments of the disclosure may include one or more of the following aspects.

In accordance with one embodiment, an endoscope tip assembly, may include: a ring-shaped base having a substantially cylindrical inner surface that is dimensioned to receive a distal end of an endoscope; and a collapsible umbrella extending radially out from the base, wherein the collapsible portion includes: a webbing forming a collapsible surface; and a plurality of flexible struts extending along the webbing and configured to flex to transition the collapsible umbrella between an insertion state and a withdrawal state; wherein the flexible struts are each attached to the inner surface of the base and extend from the inner surface, around an edge of the base, and radiate away from an outer surface of the base; and wherein, in the insertion state, the plurality of struts are flexed toward a direction extending substantially parallel with the outer surface of the base, and wherein, in the withdrawal state, the plurality of struts are flexed outward away from the outer surface of the base and the tip of each of the plurality of struts is pointed in a distal direction substantially parallel to the outer surface of the base.

Various embodiments of the endoscope tip assembly may include: a tip assembly wherein a force required to flex the plurality of struts to transition the collapsible portion to the insertion state is less than a force required to flex the plurality of struts to transition the collapsible portion to the withdrawal state; a tip of each of the plurality of struts is off-axis from an intermediate portion of each of the plurality of struts; at least one of the plurality of struts includes one or more notches located along a distal-facing surface of the strut; and a base that is substantially rigid.

Various embodiments of the endoscope tip assembly may include: an inner surface of a base including at least one crush rib projecting from the inner surface; webbing that is pleated; an outer surface of the base that includes at least one gripping structure; and an outer surface of the base that includes at least one self-locking window.

Various embodiments of the endoscope tip assembly may include: a base including a shaft sleeve, a sleeve lock, and a strut support ring; and a base including a distal cap and a shaft sleeve.

Additional objects and advantages of the embodiments will be set forth in part in the description that follows, and in part will be obvious from the description or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate the disclosed embodiments and, together with the description, serve to explain the principles of the disclosed embodiments. In the drawings:

FIG. 7B illustrates an exemplary endoscope tip assembly mounted on an endoscope in a withdrawal state, according to an embodiment of the disclosure;

FIG. 9B illustrates an endoscope, equipped with a balloon, inside of a colon;

FIG. 19A illustrates an exemplary endoscope tip assembly in a resting position, according to an embodiment of the disclosure;

FIG. 19B illustrates an exemplary endoscope tip assembly mounted on an endoscope in a resting position, according to an embodiment of the disclosure;

DETAILED DESCRIPTION

Figure 1:
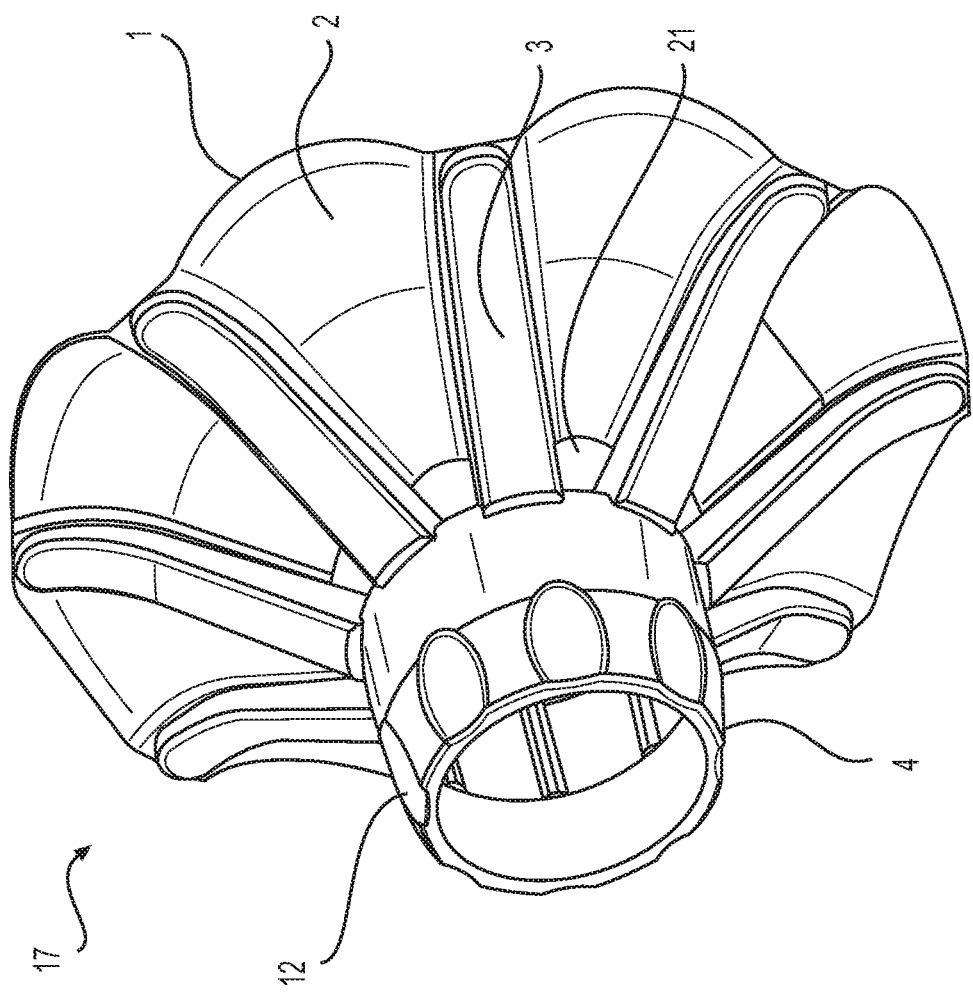
FIG. 1 illustrates an exemplary endoscope tip assembly, with pleated webbing, according to an embodiment of the present disclosure.

Reference will now be made in detail to the exemplary embodiments of the present disclosure described below and illustrated in the accompanying drawings. Wherever possible, the same reference numbers will be used throughout the drawings to refer to same or like parts.

For purposes of this disclosure, an "endoscope" may refer to any suitable type of scope for insertion into a patient during a medical procedure. Endoscopes may include, for example, colonoscopes, duodenoscopes, gastroscopes, sigmoidoscopes, enteroscopes, ureteroscopes, and bronchoscopes. The term "procedure" broadly refers to the insertion of an endoscope into a patient for any purpose, including, but not limited to, surgery, biopsy, diagnosis, treatment, visualization, implantation or removal of a device, suction, or insufflation.

Prior to providing a detailed description, the following overview generally describes the contemplated embodiments. Endoscope tip assembly 17 of the current disclosure is configured to attach to a distal end of an endoscope and to assume a streamline profile upon insertion of the endoscope within a body lumen and to assume an expanded configuration upon withdrawal of the endoscope to enlarge the body lumen to facilitate inspection of a region of interest.

Endoscope tip assembly 17 includes an attachment base 4. Base 4 is configured to receive a distal end of an endoscope so that an inner surface of base 4 attaches to an outer tip of the endoscope. Accordingly, base 4 may be sized so that the inner diameter is slightly larger than the diameter of the endoscope tip and has a complimentary shape. Specifically, base 4 is configured to be received on a rigid tip of an endoscope, as discussed further below, and may be slid, twisted, or friction-fit into place. The outside surface of the base may serve as a support for the bottom surface of the struts on withdrawal, as explained further below.

Base 4 may be present as a single unit attached to struts 3 and webbing 2, as discussed below. Base 4 may include separate parts, for example shaft sleeve 22 and sleeve lock 23, discussed below. Alternatively, base 4 may include shaft sleeve 30 and sleeve lock 25. In another embodiment, base 4 may include shaft sleeve 27, sleeve lock 26, and strut support ring 28. In a further embodiment, base 4 may include shaft sleeve 27 and distal cap 29. In the aforementioned embodiments, the components work cooperatively to provide support to struts 3 and webbing 2 and to firmly grip the tip of the endoscope, to prevent endoscope tip assembly from dislodging during a procedure.

Base 4 may include a plurality of gripping windows 19 or a plurality of pressure pads 24. Upon withdrawal, struts 3 may bear or press on gripping windows 19 or pressure pads 24. As struts 3 apply pressure to either gripping windows 19 or pressure pads 24, that force may increase the sliding friction between either gripping windows 19 or pressure pads 24 and the outer surface of the rigid tip of an endoscope. This self-locking action leading to increased friction may aid in preventing endoscope tip assembly 17 from disengaging from an endoscope during a procedure.

Webbing 2 with thickened struts 3 cooperatively define a collapsible umbrella portion extending out from base 4. Struts 3 may extend from base 4 and may be configured to flex relative to base 4 in order to assume a more streamlined, collapsed profile upon insertion into a body lumen and an enlarged, expanded profile upon withdrawal. In the collapsed configuration, struts 3 may be configured to fold so that they are substantially parallel with an axis of the endoscope to which endoscope tip assembly 17 is attached. In the expanded configuration, struts 3 may be configured to extend away from the endoscope's axis and towards the periphery of the body lumen in order to gently push on the body lumen into which the endoscope is inserted. Accordingly, when expanded, struts 3 may apply pressure to the circumference of the body lumen in order to enlarge the body lumen in the region surrounding endoscope tip assembly 17.

Struts 3 extend along webbing 2, forming a surface that connects struts 3 with one another, similar in manner to how the material of an umbrella extends between the ribs of an umbrella. Webbing 2 may extend along all or along a portion of the length of struts 3. Webbing 2 may extend all the way down the length of struts 3 to connect with base 4; webbing 2 may lie flush with the tips of struts 3; webbing 2 may cover only a portion of the struts leaving a length 31 between the tips of struts 3 and the distal edge of webbing 2; or may extend beyond the tips of struts 3.

By extending between the tips of struts 3 and connecting struts 3 with one another, webbing 2 distributes the force applied to the body lumen by struts 3 more evenly across a larger surface area when in the expanded configuration. Instead of struts 3 applying elevated pressure to the body lumen, which may cause trauma to the lumen, webbing 2 and struts 3 cooperatively create a continuous contact surface over which the force of expanded struts 3 is distributed along the periphery of the body lumen. Accordingly, instead of resulting in a few high-pressure contact regions centralized around the contact area of struts 3, the disclosed device creates a larger, diffuse, lower-pressure contact region similar to that of some balloon devices. For example, the combined calculated area of the eight struts 3 in the depicted embodiment may be approximately 480 mm$^2$, and the calculated total area of webbing 2 may be approximately 1670 mm$^2$. However, passive endoscope tip assembly 17 lacks the technical limitations and difficulties of such active balloon devices. Exemplary embodiments and details of endoscope tip assembly 17 are described further below.

Reference is now made to FIG. 1, which illustrates an exemplary endoscope tip assembly 17, in a resting state, in accordance with an embodiment of the disclosure. Endoscope tip assembly 17 includes base 4. As discussed above, base 4 may be configured to fit onto and attach to a distal end of an endoscope. Base 4 is designed to prevent endoscope tip assembly 17 from detaching from an endoscope when maneuvered within a body lumen during use. To this end, base 4 may include texturing, protrusions, and/or pressure points, for example, to increase friction between an inner surface of base 4 and an outer surface of the endoscope tip.

As shown in FIG. 1, an exemplary endoscope tip assembly 17 may include one or more crush ribs 11. Crush ribs 11 may protrude from the inner surface of base 4 to contact the endoscope and may increase contact pressure between base 4 and the endoscope tip, thereby increasing sliding friction to prevent endoscope tip assembly 17 from disengaging from the endoscope during a procedure. Crush ribs 11 may extend along an axis of base 4 or may extend at an angle to or perpendicular to the axis. Crush ribs 11 may include a plurality of discrete ribs or may extend from one end of base 4 to the other or around the full circumference of base 4. In some embodiments, crush ribs 11 may form a circular or screw-like design around the circumference of base 4. In some embodiments, crush ribs 11 may be parallel to one another, at an angle to one another, or in any suitable arrangement to increase friction. Crush ribs 11 may taper at one end, e.g., the proximal end, into a funnel or conical shape, which may facilitate engagement with the rigid distal portion of the endoscope to which it is attached. Further, crush ribs 11 may be solid or hollow or may have both solid and hollow regions.

Crush ribs 11 may be configured to deform slightly upon engagement with the endoscope or when pressure is applied to endoscope tip assembly 17 during removal of the device from the endoscope or during withdrawal of the endoscope in the body. Crush ribs 11 may be formed of any suitable material, discussed below. Crush ribs 11 may protrude from an inner surface of base 4 a suitable amount, for example, ranging from about 0.2 mm to about 0.7 mm. The inner diameter including crush ribs 11 may be smaller than the outer diameter of the scope, discussed below. The inner diameter including crush ribs 11 of endoscope tip assembly 17 may accordingly range from about 12.75 mm to about 15 mm for an adult device, and from about 8.75 mm to about 12 mm for a pediatric device, depending on the durometer of the material(s) that base 4 and crush ribs 11 are made of. Without crush ribs 11, base 4 may have a diameter ranging from about 12.25 mm to about 15 mm for an adult device, and from about 8.25 mm to about 12 mm for a pediatric device. The inner diameter of base 4 may be the same diameter as the surface upon which crush ribs 11 are attached, such that the two surfaces are flush. In another embodiment, the inner diameter of base 4 may be a different diameter than the diameter of the surface upon which crush ribs 11 are attached. Exemplary material(s) that may be used to form base 4 and crush ribs 11 include thermoplastic elastomers (e.g., polyurethane or santoprene), thermosets (e.g., rubber and silicone rubber), or any other suitable material. The hardness durometer of the material(s) that base 4 and crush ribs 11 are formed of may range from about 20 A to about 70 A.

Alternatively, an inner surface of base 4 may be substantially smooth or may include a textured pattern that extends across the inner surface of base 4 and may not include crush ribs 11. For example, the inner surface may include a coating or texturing that maintains the placement of endoscope tip assembly 17 on an endoscope. In some embodiments, base 4 and/or an inner surface of base 4 may be formed of a material with a higher coefficient of friction. Or, in some embodiments, the smooth or textured surface may further include one or more crush ribs 11.

An outer surface of base 4 may include one or more ridges, protrusions, indents, and/or textures to assist a clinician with attaching and removing endoscope tip assembly 17 from an endoscope. For example, as is shown in FIG. 1, base 4 may include one or more dimples 12 located around the outer perimeter of base 4. Dimples 12 may aid the clinician in gripping base 4 when endoscope tip assembly 17 is installed onto or removed from an endoscope.

The overall size and shape of base 4 may be based on the size and shape of the distal end of the endoscope on which tip assembly 17 is configured to attach. Exemplary endoscopes may range in diameter from approximately 13 mm to about 15 mm for adult endoscopes, while a pediatric endoscope may have a tip diameter ranging from about 9 mm to about 12 mm. In some embodiments, the inner diameter of base 4 may be between about 10 mm and about 14 mm. Further, the outer diameter of base 4 may be configured to protrude only slightly from the surface of the endoscope onto which it fits so as to not substantially increase the diameter of the endoscope tip in order to facilitate insertion when the endoscope tip assembly 17 is in the collapsed, insertion configuration. For example, the outer diameter of base 4 may be about 11 mm to about 17 mm. In some embodiments, base 4 of endoscope assembly 17 may come in a variety of sizes, for example, depending on the size and/or type of endoscope that the device is intended for use with.

Base 4 may be dimensioned so that when mounted on an endoscope, endoscope tip assembly 17 engages only a distal-most portion of the endoscope. The distal-most ends of many endoscopes include a rigid cylindrical tip, which may be made of rigid plastic or metal, to define the end of the endoscope, provide rigidity, and/or to encase or protect the optics and other structures located on the distal face of the endoscope. The bending portion of the endoscope is generally located proximal to this distal metal ring. The bending portion of most endoscopes is more flexible and is generally made of more delicate materials. It may thus be easier to puncture or damage this bending portion, which may cause leakage or may otherwise damage or compromise the integrity of the endoscope. Given the expense of endoscopes, this would be undesirable and, if the damage occurs during use, this may interrupt or render the ongoing procedure impossible.

Accordingly, it may not be desirable to slide an endoscope accessory over the bending portion or otherwise affix a device directly to the bending portion of an endoscope, either on a regular or occasional basis. To ameliorate this problem, endoscope tip assembly 17 is designed to interact with the rigid tips of endoscopes rather than the more-delicate bending portions. Thus, base 4 may be dimensioned so as to fit on the rigid-tip portion of an endoscope without overlapping onto the bending portion. Additionally, because endoscope tip assembly 17 sits at the distal tip of an endoscope, this may provide better visibility since the body lumen may be expanded at a region closer to the distal face of the endoscope where the optics are located.

Yet other devices typically are designed to affix to the bending portion in order to prevent them from disengaging from the endoscope during use. It was generally thought that an endoscope accessory should interact with and affix to more than simply the tip of an endoscope in order to keep the accessory in place. While other devices may be configured for placement further back on endoscopes or may assume a wider dimension to increase the contact area with the endoscope to resist detachment during use, embodiments of the disclosed device may be more narrow and configured to contact the distal, rigid ridge predominantly or exclusively while remaining in place on the endoscope. This may be achieved via, e.g., the use of crush ribs 11 and/or other designs, as will be discussed further below. In some embodiments, the intended placement of endoscope tip assembly 17 on only the rigid portion of the endoscope may allow for the provision of a tighter friction-fit because the design does not need to account for the delicateness of the bending portion. This may also allow base 4 to be more rigid. The rigidity of base 4 may also aid with removal by allowing a clinician to grip and apply pressure to the assembly without also applying pressure to the underlying endoscope and increasing friction between endoscope tip assembly 17 and the endoscope.

Endoscope tip assembly 17 includes a collapsible umbrella extending radially out from base 4. The umbrella is formed of webbing 2 and a plurality of flexible struts 3 configured to flex to transition the collapsible umbrella between the insertion, resting, and withdrawal states.

Endoscope tip 17 assembly may include anywhere from about one to about twenty struts 3 attached to base 4. For example, there may be three, four, five, six, eight, or twelve struts 3 attached to base 4. Struts 3 are flexible and are configured to flex between a resting position, an insertion position, and a withdrawal position. In the insertion position, shown in FIG. 7A, struts 3 are configured to flex in a proximal direction along the axis of the endoscope. This results in a streamlined profile for facilitating insertion of the endoscope into the body. Once inserted into a body lumen and guided to a region of interest, the endoscope may be slowly withdrawn to visualize the region of interest. As the endoscope is withdrawn, struts 3 may engage the body lumen and flex out from the axis of the endoscope. As the endoscope is further withdrawn, struts 3 may bend until the tips of struts 3 point in a distal direction, as shown in FIG. 8. This is the withdrawal position. When not in use, endoscope tip assembly 17 may assume a resting position, as shown in FIG. 1, in which struts 3 are biased to flare out from the axis of the endoscope. The natural outward biasing of struts 3 in the resting position may facilitate the transition between the insertion and the withdrawal position inside the body lumen.

In some embodiments, when endoscope tip assembly 17 is in a resting position, the total strut span may range from about 30 mm to about 70 mm. When endoscope tip assembly 17 is in the insertion position, the total strut span may range from about 12 mm to about 18 mm. The aforementioned strut span ranges may vary depending upon the procedure and the patient. For example, the average diameter of the upper gastrointestinal tract lumen may be different from the average diameter of the lumen of the lower gastrointestinal tract or of other body lumens. Additionally, the average diameter of the same body lumens in an infant or youth may be different than that of an adult. Accordingly, the strut span may reflect the intended application, or even the particular patient, as appropriate sizing of the strut span will facilitate effective engagement with the lumen without applying an undesirable amount of pressure to the lumen.

Struts 3 support webbing 2 to transition webbing 2 between a collapsed insertion state (similar in profile to a collapsed umbrella) and a flipped, withdrawal state (similar in profile to an inside-out umbrella). As previously described, webbing 2 and struts 3 work cooperatively to create a diffuse, high-surface-area, low-pressure region of contact with the body lumen when in the withdrawal state, similar in manner to how a balloon would apply pressure to a lumen. For example, reference is made to FIG. 9A. The portion of endoscope tip assembly 17 that contacts the body lumen is spread out over a greater surface area created by webbing 2 and struts 3, as opposed to, for example, the surface of struts 3 alone. The diffuse contact region in FIG. 9A created by endoscope tip assembly 17 is similar to the diffuse contact region created by an endoscope equipped with a balloon.

Figure 2:
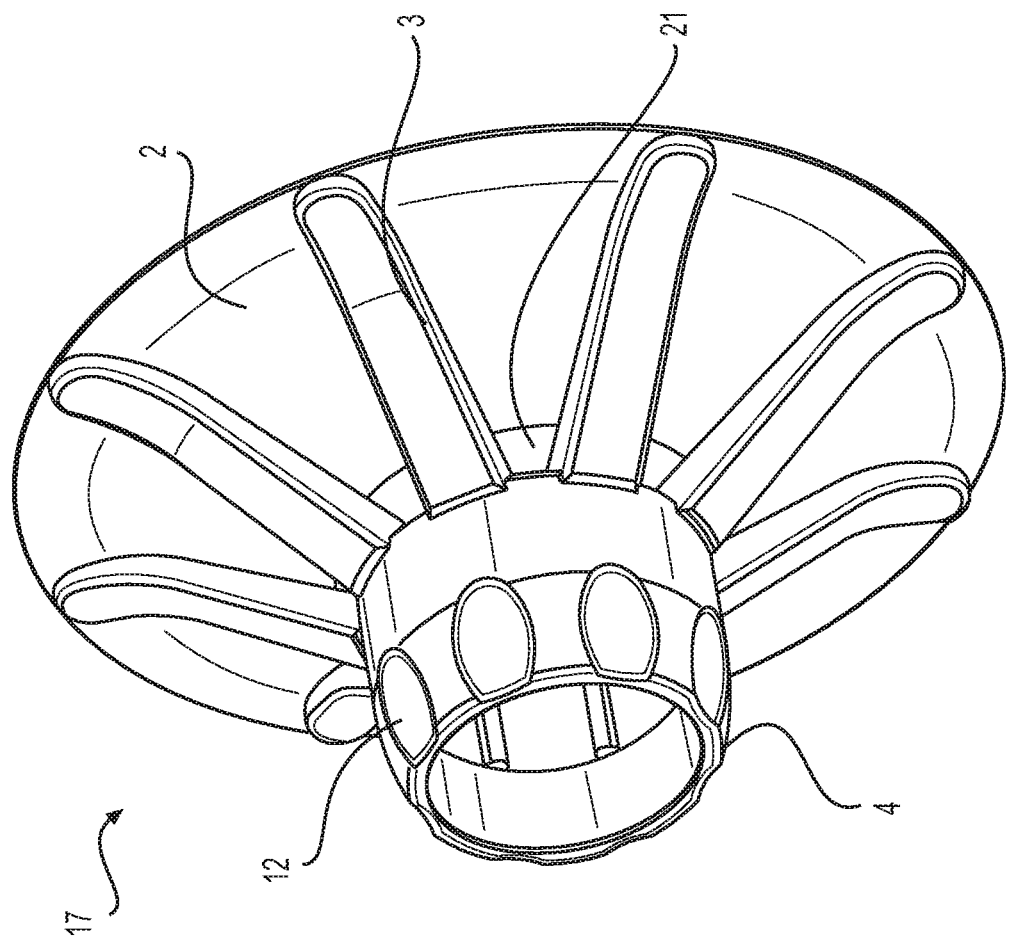
FIG. 2 illustrates an exemplary endoscope tip assembly, according to an embodiment of the disclosure.

In one embodiment, when in a resting position, there may be slack in webbing 2 between adjacent struts 3, as shown in FIG. 1, or as is shown in FIG. 2, there may be substantially no slack between adjacent struts 3. Webbing 2 may have a pleated pattern 1, as illustrated in FIG. 1, or may have a non-pleated pattern, as illustrated in FIG. 2. In either the pleated or non-pleated embodiment, webbing 2 may extend flush with the ends of struts 3, as shown in FIGS. 1 and 2, or may extend past the ends of struts 3. In some embodiments, webbing 2 may extend flush with struts 3 where it joins the ends of struts 3 but extend beyond them in a region between struts 3, or vice versa.

In one embodiment, webbing 2 and struts 3 of the collapsible umbrella may be formed of different materials. For example, webbing 2 and struts 3 may be attached to each other by an adhesive. In some embodiments, the adhesive may be an RTV (Room Temperature Vulcanizing) adhesive. In another embodiment, webbing 2 and struts 3 may be attached to each other by plastic or radio-frequency welding. In a further embodiment, webbing 2 and struts 3 may be uniformly molded. In one embodiment, webbing 2 may range from about 0.05 mm to about 0.2 mm in thickness.

In some embodiments, a gap 21 may be present in embodiments in which webbing 2 does not extend down struts 3 to meet with base 4. This gap 21 may allow fluids and gases to pass through when endoscope tip assembly 17 is in the withdrawal position when struts 3 and webbing 2 are engaged with the lumen. In other embodiments, gap 21 may be absent. In some embodiments, the distance between base 4 and the distal edge of webbing 2 may be between about 1 mm and about 6 mm.

In some embodiments, base 4 may include a plurality of dimples 12. As previously mentioned, dimples 12 may facilitate gripping of endoscope tip assembly 17 by a clinician, which may aid in the installation onto and removal from an endoscope. However, dimples 12 shown in FIG. 1 are exemplary. Any suitable design or pattern that aids a clinician in gripping endoscope tip assembly 17 is contemplated by this disclosure, such as, for example, ridges, grooves, or a textured finish or material on an outer surface of base 4.

Webbing 2, struts 3, base 4, or crush ribs 11 may be made of the same material or different materials. Suitable materials include, thermosets (e.g., rubber or silicon rubber), thermoplastic elastomers (e.g., thermoplastic polyurethane or santoprene, or other suitable biocompatible materials. Webbing 2 may also be made of thermoplastic polyurethane film, any suitable polymer, or any suitable biocompatible materials. One or more of webbing 2, struts 3, base 4, or crush ribs 11 may also include a suitable coating, e.g., a lubricious or anti-bacterial coating.

Figure 3:
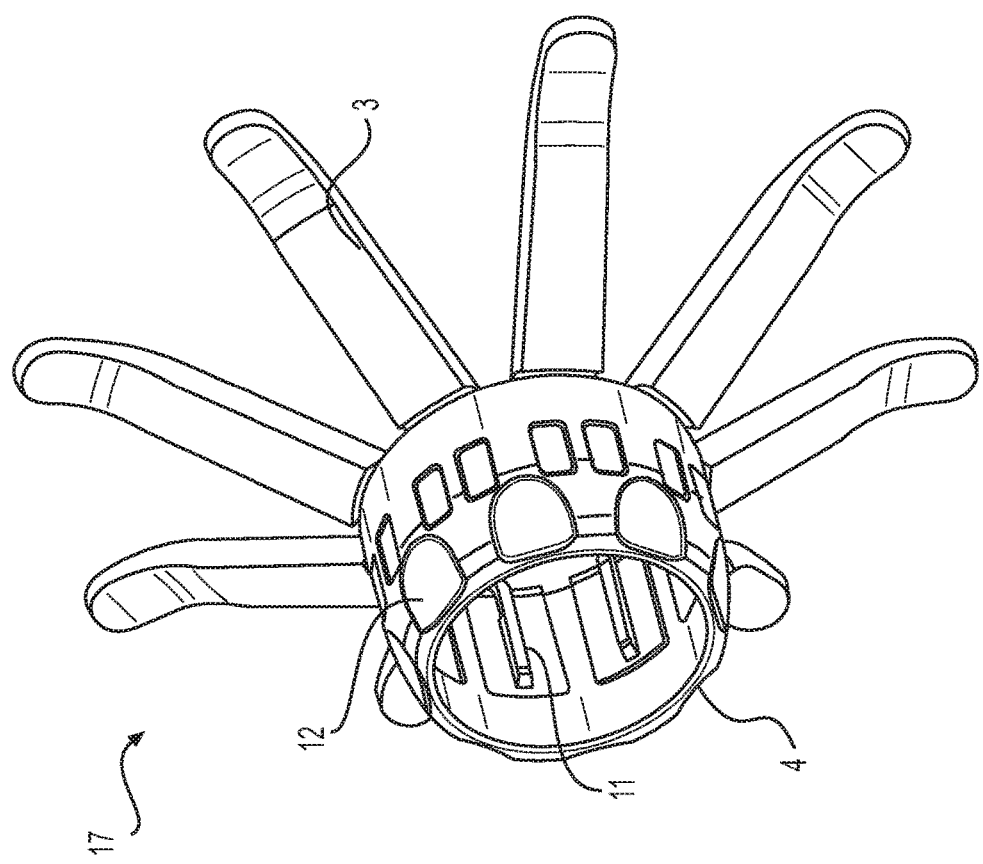
FIG. 3 illustrates an exemplary endoscope tip assembly, with the webbing removed for clarity, according to an embodiment of the disclosure.
Figure 4:
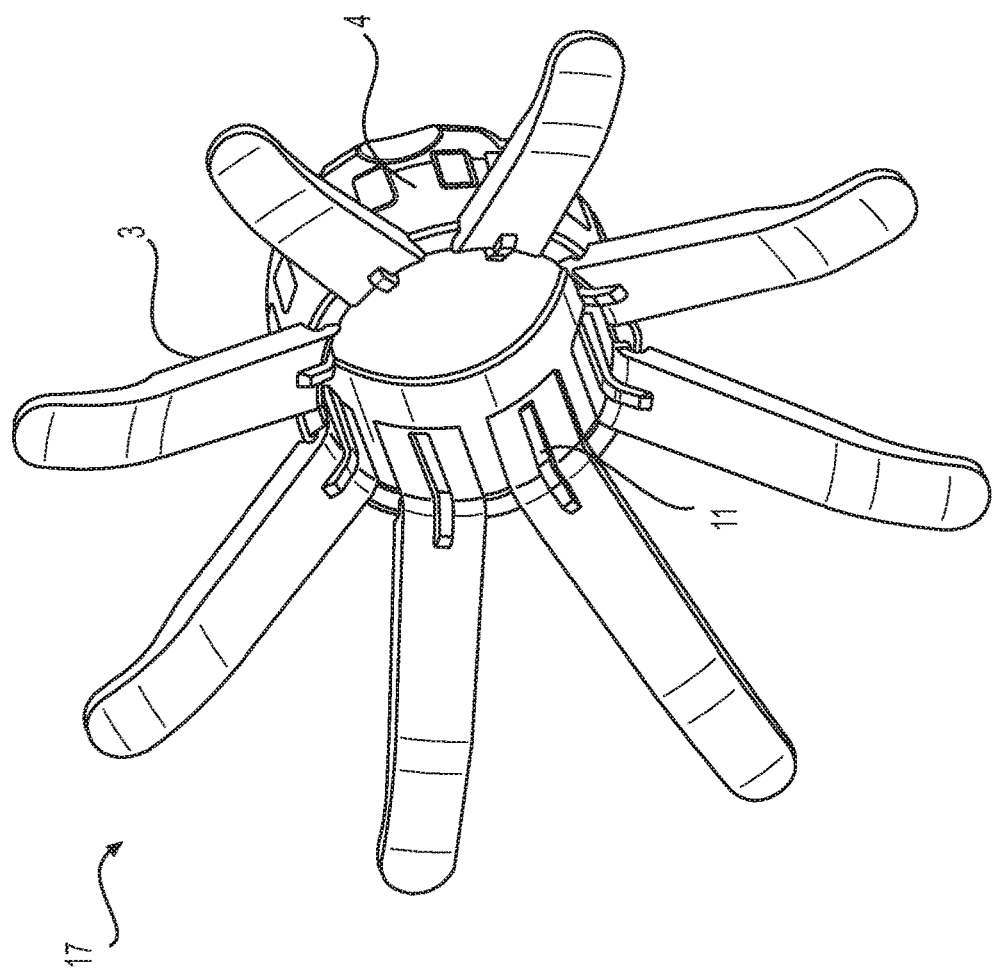
FIG. 4 illustrates an exemplary endoscope tip assembly, with the webbing removed for clarity, according to an embodiment of the disclosure.

Reference is now made to FIG. 3 and FIG. 4, which illustrate distal and proximal views, respectively, of endoscope tip assembly 17, drawn without webbing 2 for clarity, according to another embodiment of the disclosure. In these views, the inner surface of an exemplary base 4 can be viewed more clearly. As shown, struts 3 are attached to base 4 at an inner surface of base 4. Struts 3 extend from the inner surface of base 4, over an edge of base 4, and flare outwards from base 4 to their tips. Struts 3 may be more flexible than base 4, which, in some embodiments, may be rigid. The attachment of struts 3 to base 4 will be described in detail further below. As discussed previously and shown here in more detail, crush ribs 11 may increase the sliding friction between the rigid endoscope tip and endoscope tip assembly 17. Crush ribs 11 are exemplary; other means for increasing sliding friction are contemplated, as discussed above, including, for example, ridges, or texturing.

In some embodiments, the struts 3 may be more flexible than base 4, which may be rigid. In some embodiments, the struts may be made out of silicone and the base 4 may be made out of polycarbonate or polysulfone. These materials are of substantial rigidity, are of medical grade, are capable of being injection molded, and have a high glass transition temperature to allow for quick curing of silicone struts during silicone overmolding.

Crush ribs 11, if included, may extend along struts 3, between struts 3, or both. They may be separate from struts 3 and/or base 4, or may be formed as part of one or the other, or both, e.g., in the event that all three are formed of one material. Further, as shown in FIG. 4, crush ribs 11 may extend along a surface of struts 11 where the base of struts 11 attach to and project out from the inner surface of base 4. In such an embodiment, crush ribs 11 may form a funnel for easier engagement with the scope tip. In some embodiments, crush ribs 11 may be made of the same material as base 4 and/or struts 3. In other embodiments, crush ribs 11 are made of a different material than crush ribs 11 and/or struts 3.

Figure 5:
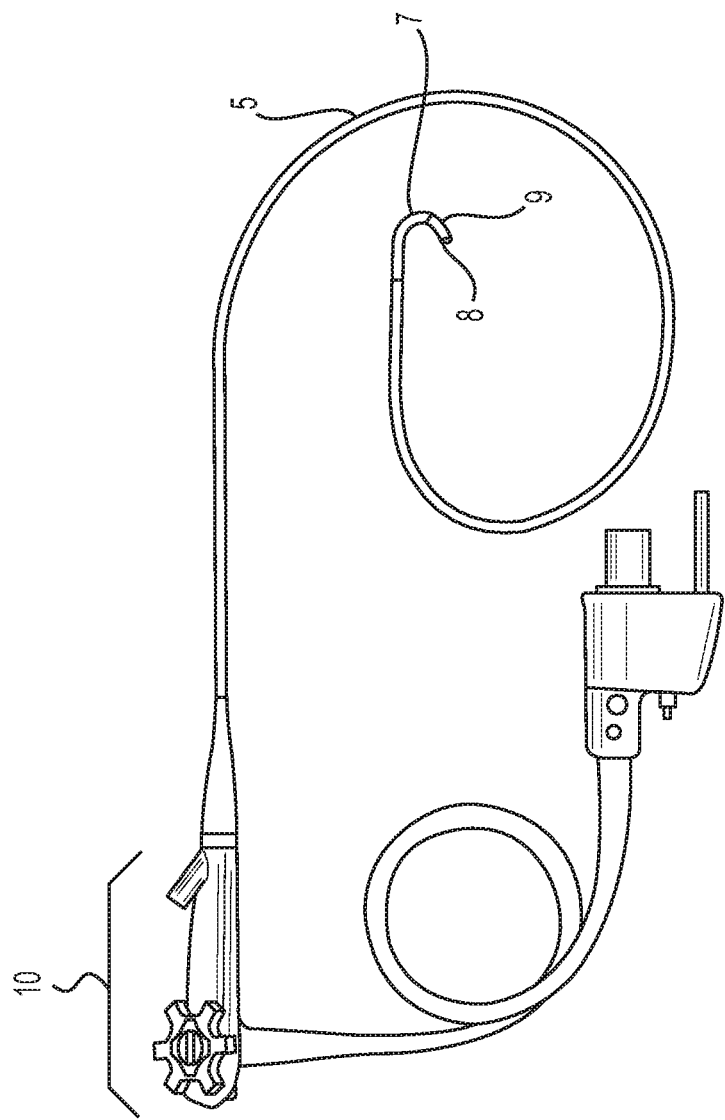
FIG. 5 illustrates an exemplary endoscope for receiving an endoscope tip assembly.

Reference is now made to FIG. 5, which illustrates a generic endoscope device 10. An endoscope control portion 6 may include the knobs and dials that a clinician uses to guide tip 9 in a patient through controlled bending of bendable portion 7, found at the distal region of an insertion tube 5. Insertion tube 5 is a long, flexible tube that bends as endoscope 10 is inserted into a patient. Bendable portion 7 is controlled, remotely, by a clinician and bends to navigate the turns of a lumen. Rigid tip 9, the distal-most portion of the endoscope 10, houses, e.g., a camera face 8. Rigid tip 9 is where endoscope tip assembly 17 of the present disclosure may be affixed. Endoscope tip assembly 17 of the present disclosure may not extend onto bendable portion 7, as extending onto said portion may interfere with the clinician's ability to control the bending of portion 7 or may harm bending portion 7, as described above.

Figure 6:
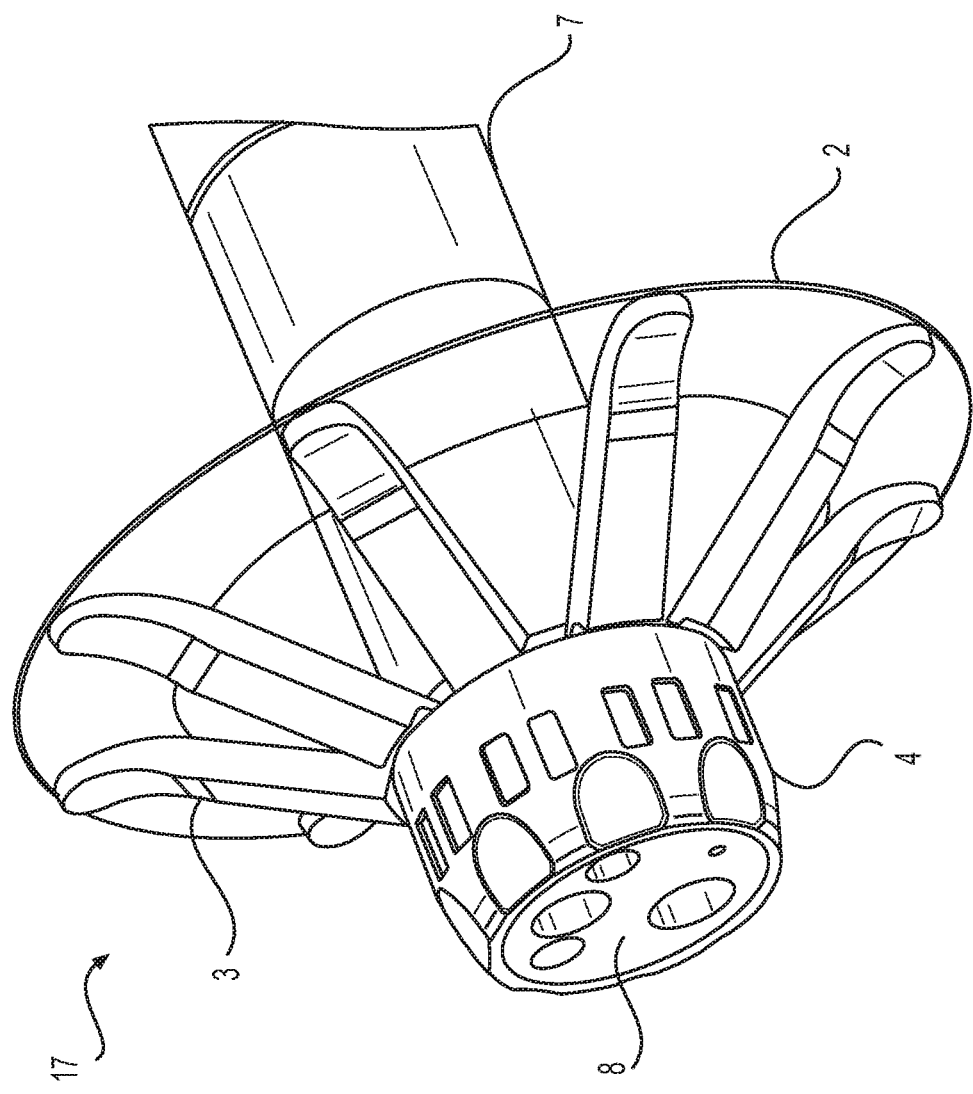
FIG. 6 illustrates an exemplary endoscope tip assembly mounted on an endoscope in a resting position, according to an embodiment of the disclosure.

Reference is now made to FIG. 6, which illustrates endoscope tip assembly 17 mounted on an endoscope 10, in a resting state, according to an embodiment of the disclosure. In this embodiment, the distal edge of base 4 is flush with a camera face 8 of endoscope 7. This position may help to ensure that endoscope tip assembly 17 sits only on ring 9 and may not interfere with the operation of bendable portion 7 of endoscope 10, although, in some embodiments, base 4 may be set back slightly from the face of the endoscope. In some embodiments, the angle between struts 3 and the longitudinal axis of endoscope 7 may be between about 45° and about 90° in the resting state.

Figure 7A:
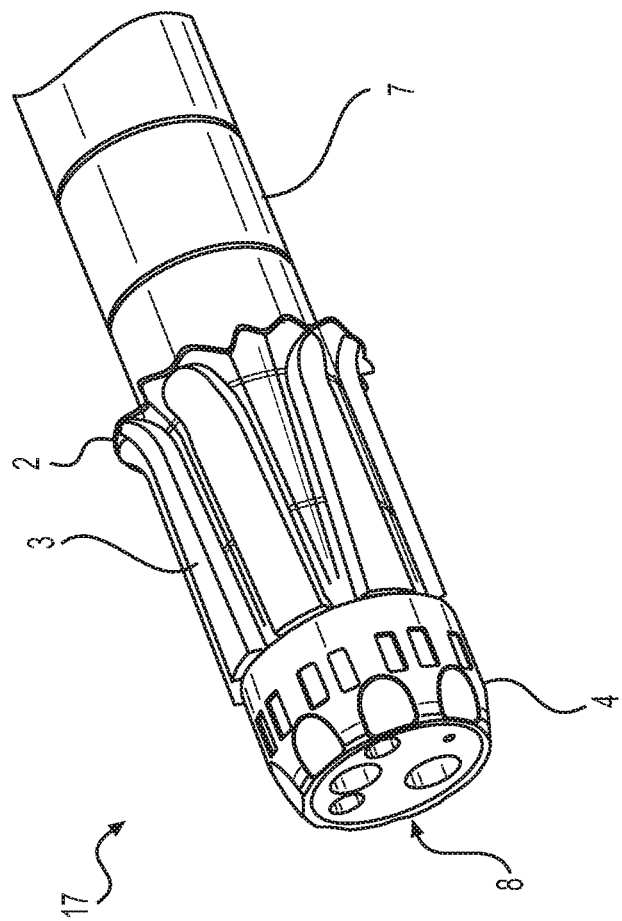
FIG. 7A illustrates an exemplary endoscope tip assembly mounted on an endoscope in an insertion position, according to an embodiment of the disclosure.
Figure 8:
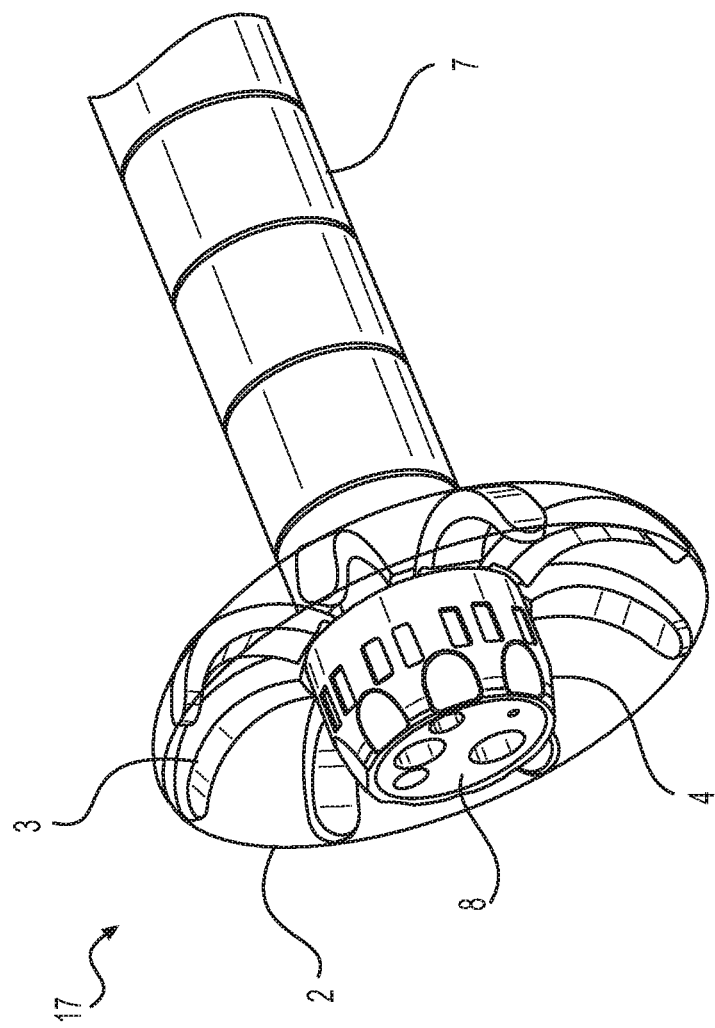
FIG. 8 illustrates an exemplary endoscope tip assembly mounted on an endoscope in a withdrawal position, according to an embodiment of the disclosure.

Reference is now made to FIG. 7A, which illustrates an endoscope tip assembly mounted on endoscope 10, in the insertion state. In some embodiments, the angle between struts 3 and a longitudinal axis of endoscope 10 may be between about 0° and about 45°. It is advantageous for struts 3 and webbing 2 to collapse into this position during insertion so that a smaller overall diameter is achieved for ease of insertion. The force to flex struts 3 and webbing 2 into the insertion position may be less than the force required to flex struts 3 and webbing 2 into the withdrawal position, as discussed below. Only a portion of the thickness of each strut 3 may need to be bent to transition the strut from the resting position into the insertion position. This thickness may range from about 0.5 mm to about 1 mm. On the other hand, more of the thickness of each strut 3 or all of each strut 3 may need to be bent to invert struts 3 into the withdrawal position. This thickness may range from about 1 mm to about 3 mm.

Reference is now made to FIG. 7B, which illustrates an endoscope tip assembly mounted on endoscope 10, in a withdrawal position. When endoscope tip assembly 17 is in such a position, there may be slack in webbing 2 between struts 3, which results in a pleating or bunching of webbing 2, similar to the pleating and bunching of an umbrella in a closed position, as illustrated in FIG. 7B. In another embodiment, the pleats may be pre-formed such that pleating is present when there is no slack in the webbing.

Reference is now made to FIG. 8, which illustrates endoscope tip assembly 17 mounted on endoscope 10, in the withdrawal state. In some embodiments, the angle between struts 3 and the longitudinal axis of endoscope 7 may be between about 50° and about 180° in the withdrawal state, measured along a straight line extending from the tips of struts 3 to where they meet base 4. The diameter of the inside-out umbrella shape created by struts 3 and webbing 2 in this position may range from about 20 mm to about 30 mm.

Endoscope tip assembly 17 assumes this position upon withdrawal of the endoscope by flipping inside-out like an umbrella from the insertion position (similar in shape to a closed umbrella) depicted in FIG. 7A. Struts 3 may engage the body lumen as endoscope 10 is initially withdrawn, and this engagement in combination with withdrawal causes struts 3 to flex outwards away from the endoscope and into the withdrawal state. The inside-out umbrella shape of endoscope tip assembly 17 may contact the lumen and gently apply outward pressure to the lumen, thereby resulting in less traumatic contact with the lumen by making contact with a larger surface area across a more diffuse region, as opposed to discreet points of contact at the tips of struts 3. The contact achieved using endoscope tip assembly 17 may be similar in manner to the type of contact that would be achieved using the balloon of a balloon-equipped endoscope.

Figure 9A:
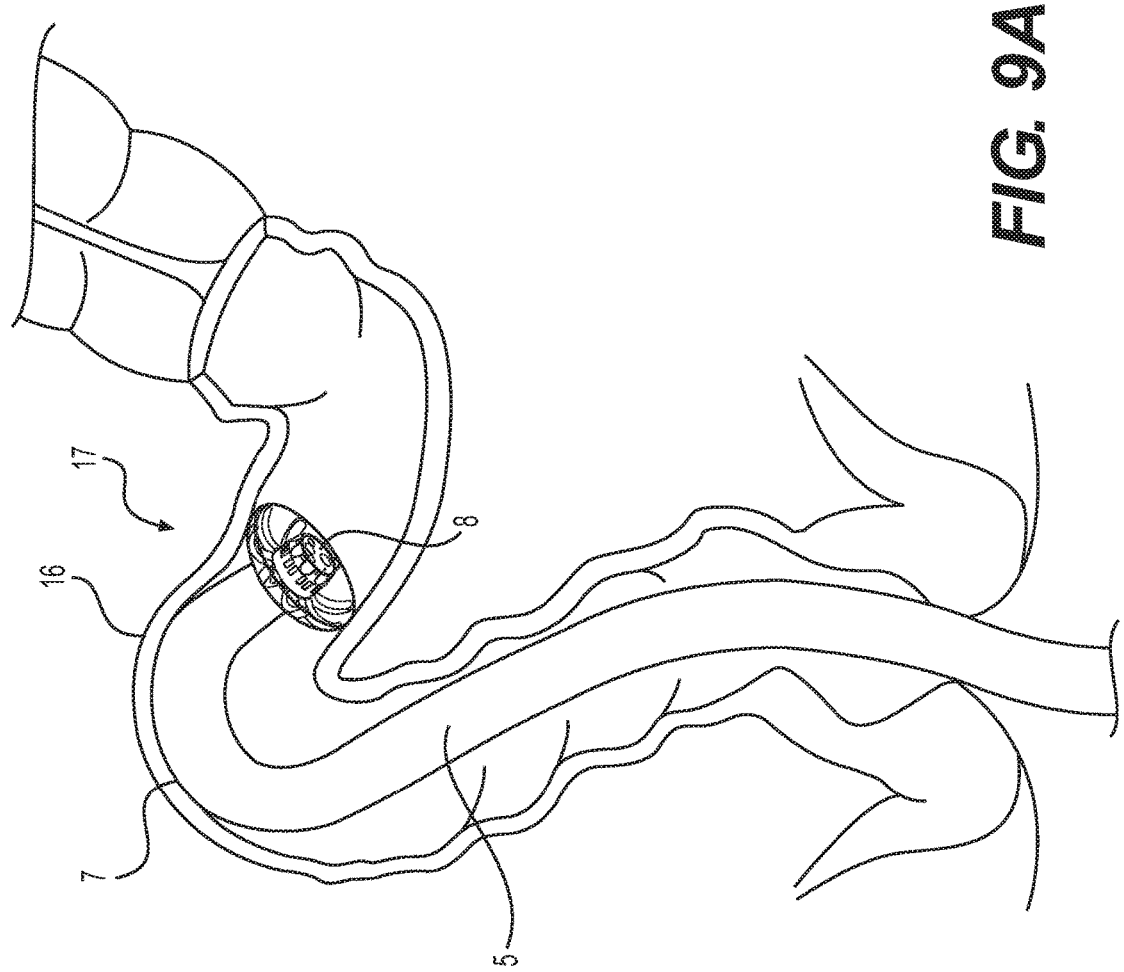
FIG. 9A illustrates an exemplary endoscope tip assembly mounted on an endoscope in a withdrawal position inside of a colon, according to an embodiment of the disclosure.

Reference is now made to FIG. 9A, which illustrates an endoscope tip assembly 17 mounted on endoscope tip 9 (obscured from view), inside of a colon 16 in a withdrawal state. The inside-out umbrella shape may lead to less traumatic contact with the colonic wall, as the outward force is evenly distributed around the perimeter of webbing 2, similarly to a balloon-equipped endoscope. As shown in FIG. 9A, in the withdrawal position endoscope tip assembly 17 applies a gentle pressure to the colon, holding the colonic folds in a more open configuration, which may improve visualization. In this manner, the shape may assist in maximizing the clinician's visualization by flattening the colonic folds, thereby revealing surfaces that may otherwise be obscured by these folds. This shape may also assist in stabilizing endoscope tip 8 so that a clinician may visually inspect the interior of the colon or perform a procedure more easily. Additionally, by expanding outwards evenly on all sides of the endoscope, struts 3 and webbing 2 may center the endoscope in a central region of the lumen, helping to at least partially counteract the force of gravity and counteract the propensity of the endoscope tip to drop along the wall of the colon or to drag along the wall of the colon during withdrawal.

Reference is now made to FIG. 9B, which illustrates an endoscope tip balloon mounted on an endoscope, inside of colon 16. Reference is made to the similarity in the diffuse contact region between the balloon and the colonic wall in FIG. 9B compared with that achieved by endoscope tip assembly 17 in FIG. 9A. However, the active balloon in FIG. 9B requires additional equipment to inflate and control the balloon, whereas the passive endoscope tip assembly 17 in FIG. 9A does not require such additional equipment or control. Also, passive endoscope tip assembly 19 is located right at the distal tip of the endoscope, whereas the axial distance from the endoscope tip to the active balloon is much larger, potentially reducing the impact that fold opening has on improved visualization behind folds.

Figure 10:
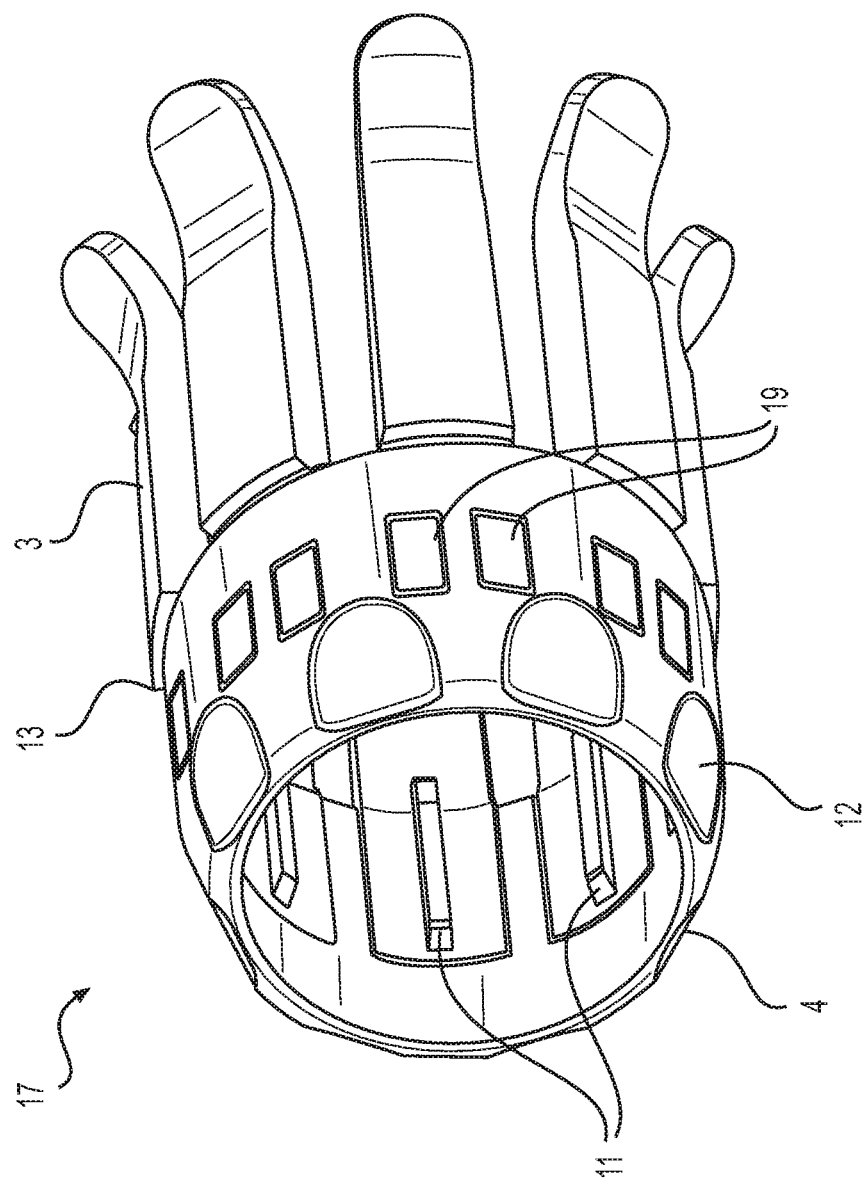
FIG. 10 illustrates an exemplary endoscope tip assembly with struts in an insertion position and the webbing removed for clarity, according to an embodiment of the disclosure.

Reference is now made to FIG. 10, which illustrates endoscope tip assembly 17 in an insertion state, with webbing 2 omitted for clarity, in accordance with an embodiment of the disclosure. The embodiment of FIG. 10 depicts a plurality of gripping windows 19. Base 4 may include any suitable number of gripping windows 19. For example, base 4 may include zero, two, four, six, eight, ten, twelve, or more gripping windows 19. In some embodiments, gripping windows 19 may provide gripping assistance to a clinician as he or she mounts and dismounts endoscope tip assembly 17. Gripping windows 19 may be located anywhere on base 4 and may be made of the same, or different, material as base 4.

Figure 11:
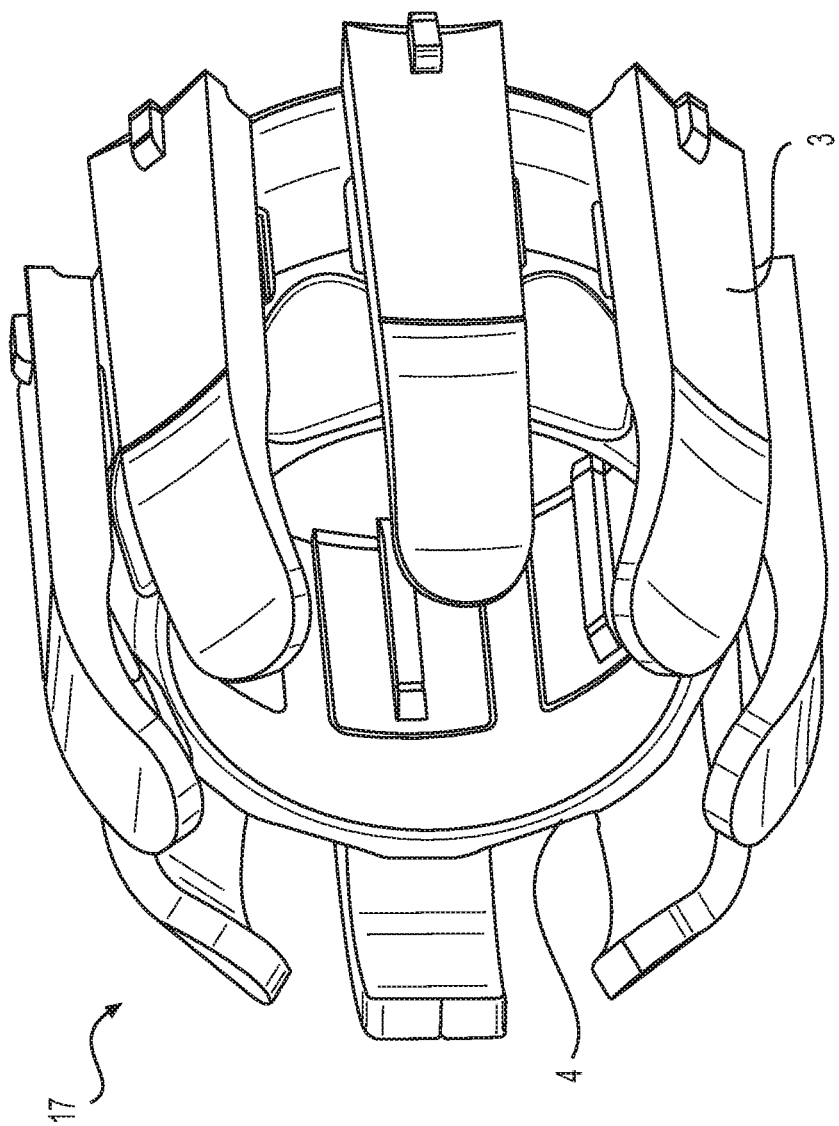
FIG. 11 illustrates an exemplary endoscope tip assembly with struts extended past the withdrawal position, and the webbing removed for clarity, according to an embodiment of the disclosure.

Reference is now made to FIG. 11, which illustrates endoscope tip assembly 17 in a position with struts 3 folded in an extreme withdrawal state, with webbing 2 omitted for clarity, in accordance with an embodiment of the disclosure. In some embodiments, it may be advantageous for endoscope tip assembly 17 to be able to assume the smallest possible outer diameter when mounted on an endoscope during withdrawal, when viewed along the longitudinal axis of the endoscope. A minimal outer diameter may be achieved by struts 3 folding toward, and potentially past, the distal end of the endoscope. This configuration may help prevent traumatic contact, for example, in a more narrow area of a body lumen, e.g., upon final removal of the endoscope tip from the anus. Accordingly, in some embodiments, struts may be able to flex in a distal direction to a position substantially parallel with an axis of the endoscope.

The force required for struts 3 to assume an insertion position, as illustrated in FIG. 10, is less than the force required for struts 3 to assume a withdrawal position, as illustrated in FIG. 8 and FIG. 11. In one embodiment, the force required for struts 3 to flex into the insertion position, as illustrated in FIG. 10, may range from about 0.3 lb to about 0.4 lb. In another embodiment, the force required for struts 3 to assume the withdrawal position, as illustrated in FIG. 11, may range from about 2.6 lb to about 3.0 lb. The ratio of withdrawal stiffness to insertion stiffness of struts 3 may range from about 5 to about 8.

Requiring a small insertion force to flex struts 3 into an insertion position may help prevent mucosal trauma during the procedure. During insertion, the endoscope tip is guided to a region of interest, and thus the goal is to achieve a streamline profile with a smaller diameter to facilitate navigation. Endoscope tip assembly 17 is thus configured to be substantially parallel to an axis of the endoscope and is not intended to apply an outward pressure to the colon to enlarge the colon in the insertion position. By contrast, during withdrawal, endoscope tip assembly 17 extends away from the axis of the endoscope to apply pressure to the colon to enlarge the colon and aid in visualization. Thus, in the withdrawal position, struts 3 must be able to resist the force of the endoscope being withdrawn and the friction applied by the body lumen as the endoscope is being withdrawn. While some flexibility in the withdrawal position may be desirable to prevent trauma to the mucosa during the procedure, if they are too flexible in the withdrawal position, then struts 3 may flex completely distally, as shown in FIG. 10, which would fail to open up the colon, may obstruct the clinician's vision, and/or may fail to stabilize the endoscope tip in the center of the colon. The fact that a larger force may be required for endoscope tip assembly 17 to flip like an inside-out umbrella from an insertion position to a withdrawal position may allow struts 3 and webbing 2 to maintain an umbrella-like shape upon withdrawal, thus helping to improve visualization and tip stabilization. In some embodiments, a small ratio of insertion force to withdrawal force may be desirable.

Figure 12:
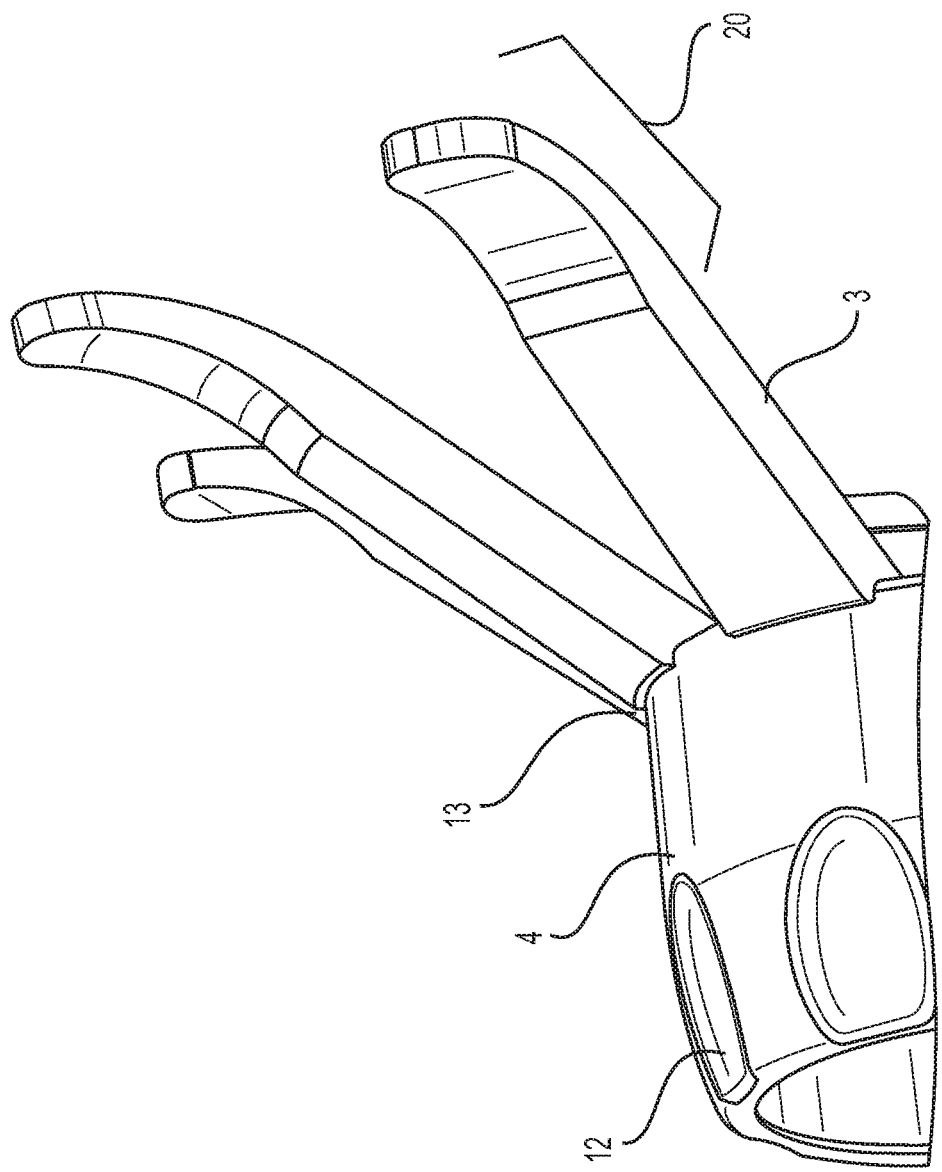
FIG. 12 illustrates a magnified view of a portion of an exemplary endoscope tip assembly with struts in a resting position, and the webbing removed for clarity, according to an embodiment of the disclosure.

Reference is now made to FIG. 12, which illustrates an enlarged side view of a portion of endoscope tip assembly 17 in a resting state, with webbing 2 omitted for clarity, in accordance with an embodiment of the disclosure. A positive stop 13 may assist strut 3 in maintaining position and shape upon withdrawal. Positive stop 13 may help struts 3 and webbing 2 maintain the inside-out umbrella shape upon withdrawal, as previously described.

Figure 13:
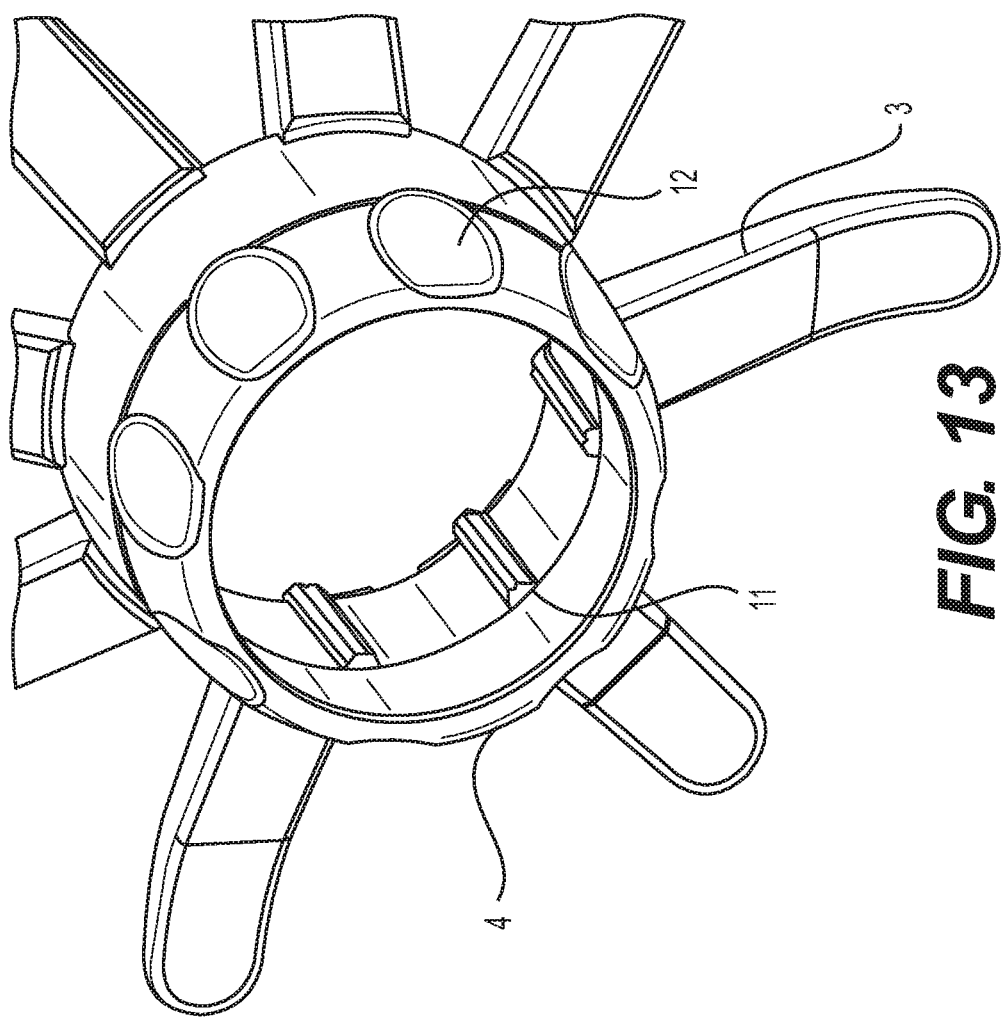
FIG. 13 illustrates an exemplary endoscope tip assembly in a resting position, with the webbing removed for clarity, according to an embodiment of the disclosure.

Reference is now made to FIG. 13, which illustrates a close-up distal view of an endoscope tip assembly in a resting state, with webbing 2 omitted for clarity, in accordance with an embodiment of the disclosure. As previously discussed, crush ribs 11 may be included on the inner surface of base 4, and they may assist in increasing the amount of sliding friction between base 4 and an endoscope, which may in turn prevent endoscope tip assembly 17 from slipping off of an endoscope during a procedure.

Figure 14:
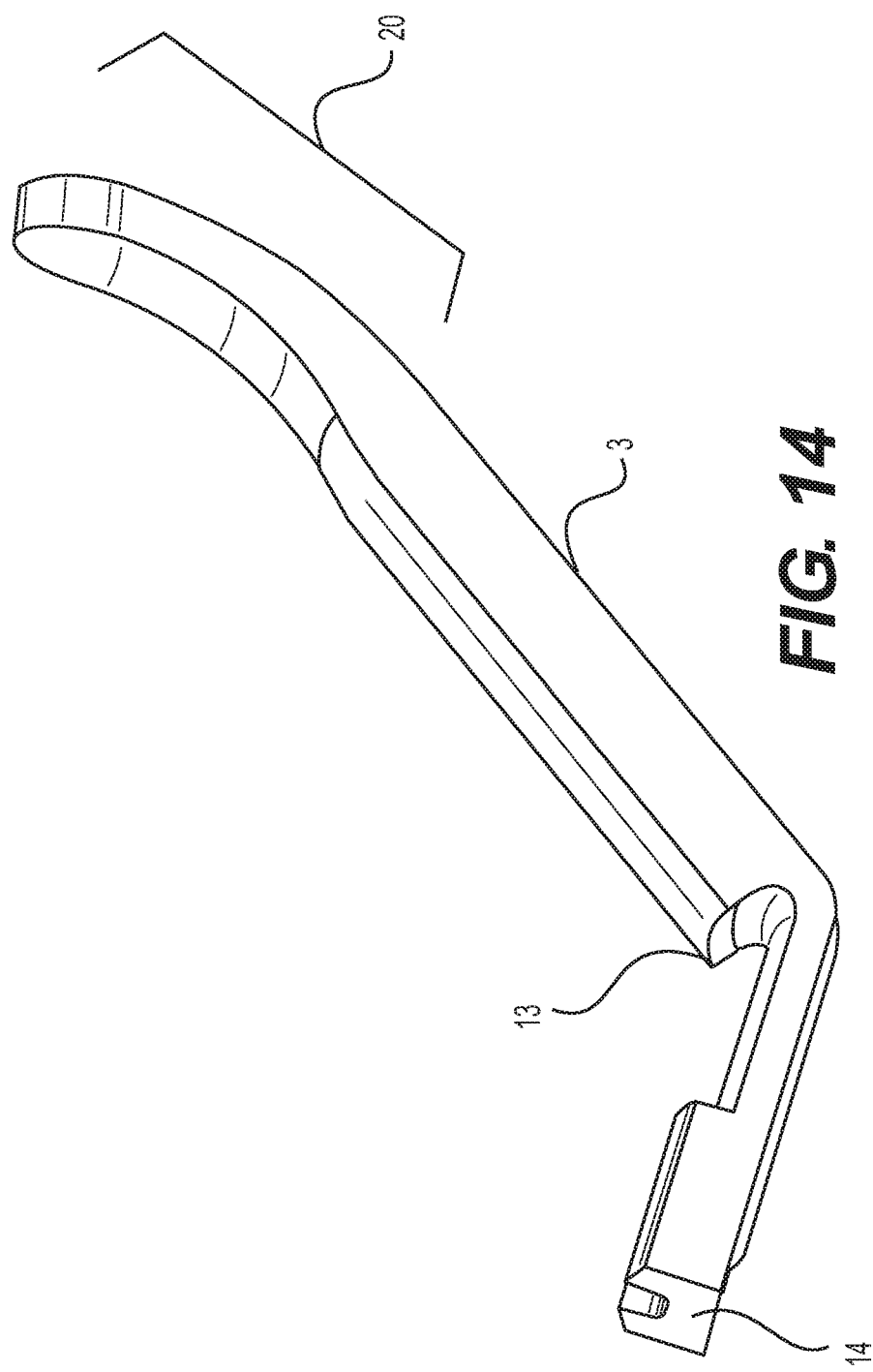
FIG. 14 illustrates an exemplary strut for an endoscope tip assembly, according to an embodiment of the disclosure.

Reference is now made to FIG. 14, which illustrates a side-view of an exemplary strut 3, in accordance with an embodiment of the disclosure. Strut 3 may exist in a variety of shapes and thickness. In some embodiments, the thickness along the length of strut 3 may vary, as indicated by tip portion 20 in FIG. 14. In some embodiments, the width of strut 3 may vary, e.g., as shown in FIG. 14, tip portion 20 may be narrower than a base-mount 14. This difference in thickness and/or width may give rise to differences in flexibility and thus, differences in forces required to flex different regions struts 3. Alternatively, the thickness and/or width may be consistent along strut 3.

In some embodiments, the thickness of the straight portion of strut 3 may range from about 0.5 mm to about 3.0 mm. In some embodiments, the thickness of tip portion 20 of strut 3 may range from about 0.5 mm to about 1.0 mm.

In some embodiments. In some embodiments, the width of strut 3 may range from about 2 mm to about 5 mm, and struts 3 may have a uniform width or may vary in width along their length.

In some embodiments, tip portion 20 of strut 3 may be angled outward. In one embodiment, the angle of tip portion 20 of strut 3 may range from about 110° to about 160°. If tip portion 20 is angled, it may help struts 3 to engage with the lumen by catching on the surface of the lumen upon withdrawal. This increased engagement may assist struts 3 and webbing 2 to flip inside-out like an umbrella and thus achieve the withdrawal state. At least in part because the thickness of each strut tip is relatively thin and the rigidity of each of the strut tip is relatively low, endoscope assembly 17 is pliable and atraumatic when engaging the lumen and when in the withdrawal state.

Struts 3 and webbing 2 are configured to make contact with the surrounding body lumen during withdrawal, in an effort to stabilize the tip of the endoscope and to improve visualization. Additionally, struts 3 must interact with the body lumen to transition from the insertion position to the withdrawal position. Therefore, the length of struts 3 is dictated, at least in part, by the diameter of the body lumen into which it will be inserted. In some embodiments, the length of struts 3 from positive stop 13 to the outermost tip may range from about 10 mm to about 25 mm.

Figure 15:
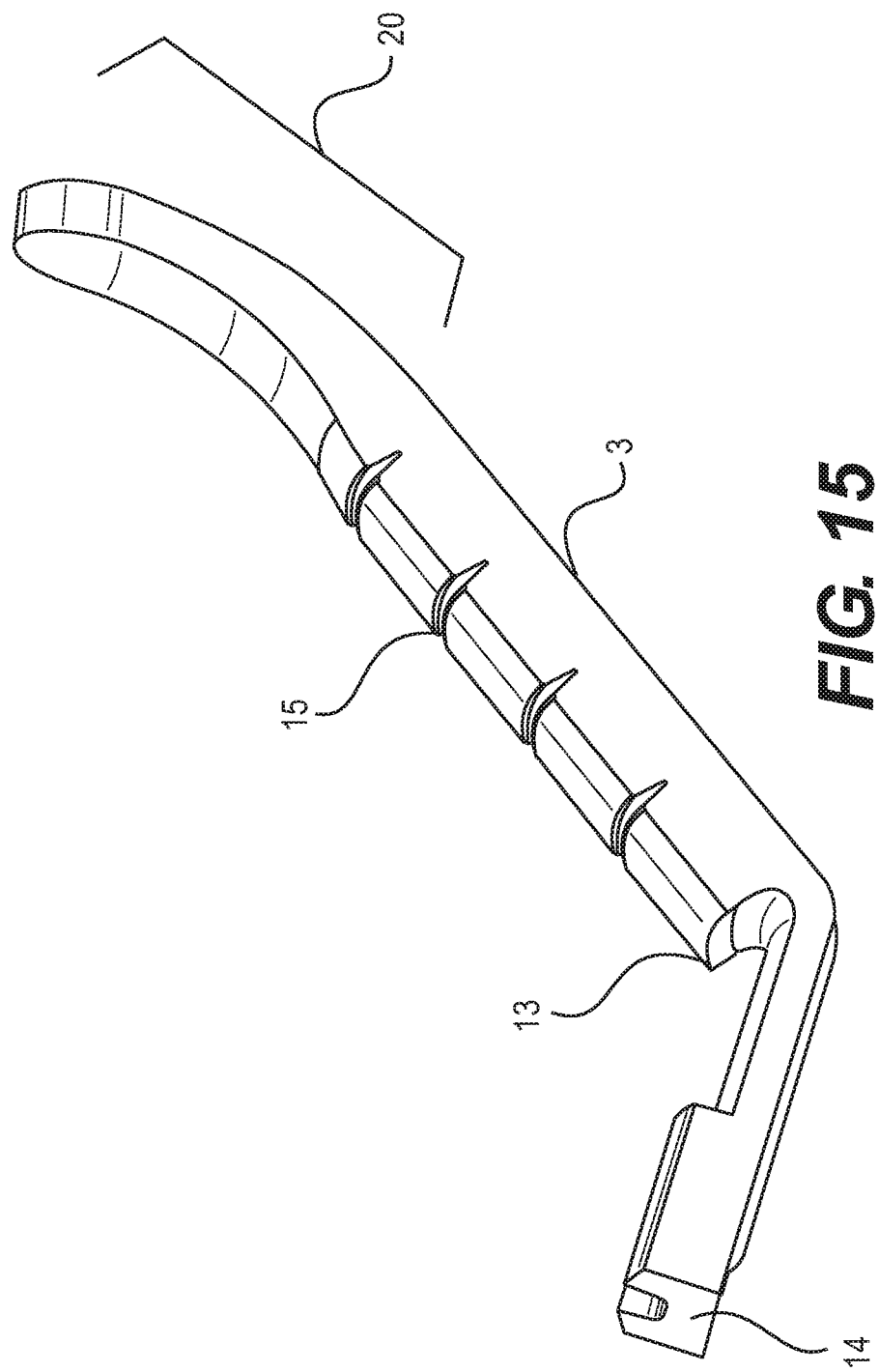
FIG. 15 illustrates an exemplary strut for an endoscope tip assembly, according to an embodiment of the disclosure.

Reference is now made to FIG. 15, which illustrates a side-view of strut 3, in accordance with an embodiment of the disclosure. In this embodiment, strut 3 includes one or more notches 15. Notches 15 may give rise to a difference in stiffness of strut 3 between a proximal-facing surface and a distal-facing surface of strut 3. For example, the surface of strut 3 with notches 15 may require less force to bend inwards on itself than a surface of strut 3 without notches 15. In some embodiments, this difference between one surface of strut 3 and the other may allow strut 3 to preferentially bend in one direction over the other.

In some embodiments, there may be one or more notches 15 in strut 3. In some embodiments, notches 15 may be located only on the straight portion of strut 3. In other embodiments, the notches may be located on both the straight portion and angled portion 20 of strut 3. In other embodiments, there may be no notches 15, as illustrated in FIG. 14. Notches 15 may have any suitable shape, e.g., slits, rectangular, triangular, U-shaped, or tapered in cross-section. The gaps formed on the notched surface allow that surface to collapse in on itself and the shape of the notches may thus affect the flexibility of strut 3.

Figure 16:
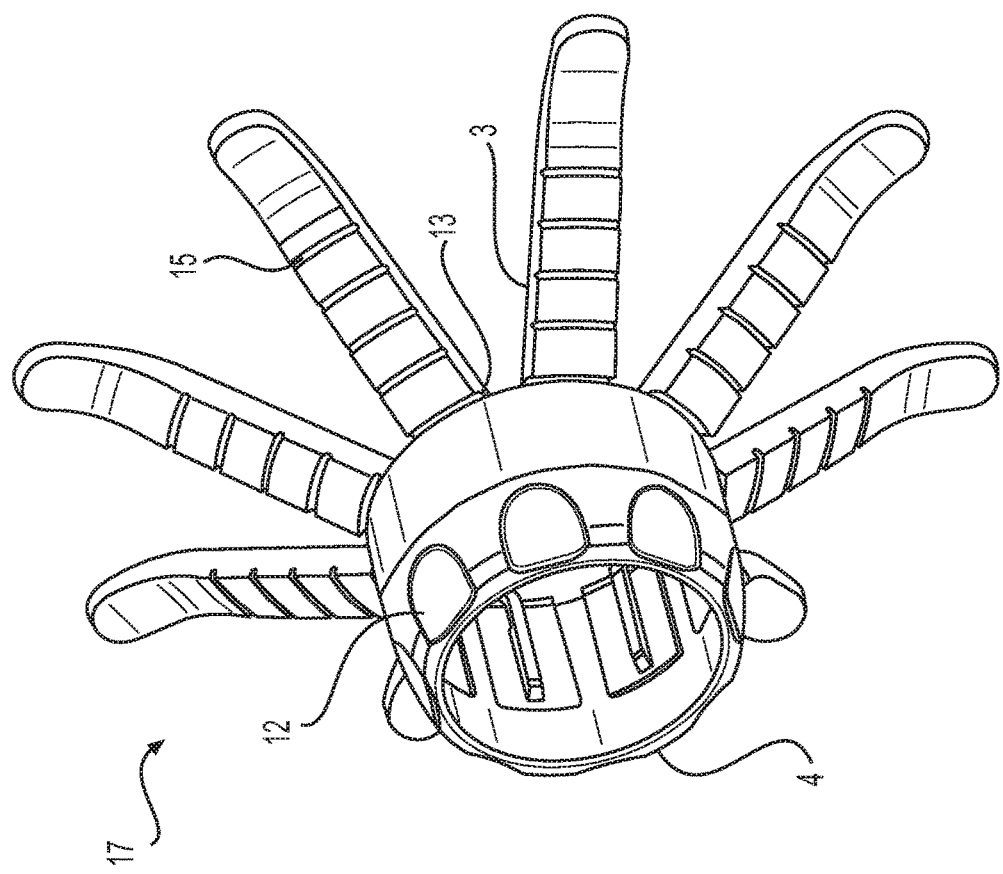
FIG. 16 illustrates an exemplary endoscope tip assembly, with the webbing removed for clarity, according to an embodiment of the disclosure.

Reference is now made to FIG. 16, which illustrates an angled view of the distal end of endoscope tip assembly 17, with notches 15 in struts 3, where webbing 2 has been omitted for clarity, in accordance with an embodiment of the disclosure. FIG. 16 illustrates that, when notches 15 are present in struts 3, struts 3 assume a resting position similar to that of struts 3 without notches, as illustrated in FIG. 3. Reference is now made to FIG. 17A, which illustrates an endoscope tip assembly 17 mounted on an endoscope 10 in a resting state, in accordance with an illustrative embodiment of the disclosure. Shaft sleeve 22 and sleeve lock 23 may work cooperatively to prevent endoscope tip assembly 7 from disengaging from an endoscope and to provide support and rigidity to struts 3 during withdrawal. Sleeve lock 23 may be tapered such that the inner diameter of the distal end may be slightly greater than the inner diameter at the proximal end. In one embodiment, the distal end of sleeve lock 23 may have a diameter ranging from about 13.8 mm to about 15.5 mm. In another embodiment, the proximal end of sleeve lock 23 may have a diameter of about 12.8 mm to about 15.0 mm. Like sleeve lock 23, shaft sleeve 22 may also be tapered, with the outer diameter of the proximal end of shaft sleeve 22 being slightly larger than the diameter of the distal end. In one embodiment, the outer diameter of the distal end may range from about 13.3 mm to about 15.5 mm. In another embodiment, the outer diameter of the proximal end may range from about 13.8 mm to about 16 mm. The tapered nature of both shaft sleeve 22 and sleeve lock 23 may aid in increasing sliding friction between shaft sleeve 22 and rigid tip 9 during withdrawal, when struts may be forced to flex in a distal direction and press on sleeve lock 23. The tapered sections may engage, increasing the pressure and friction force between shaft sleeve 22 and rigid tip 9, which may prevent endoscope tip assembly 17 from disengaging from rigid tip 9.

Figure 17B:
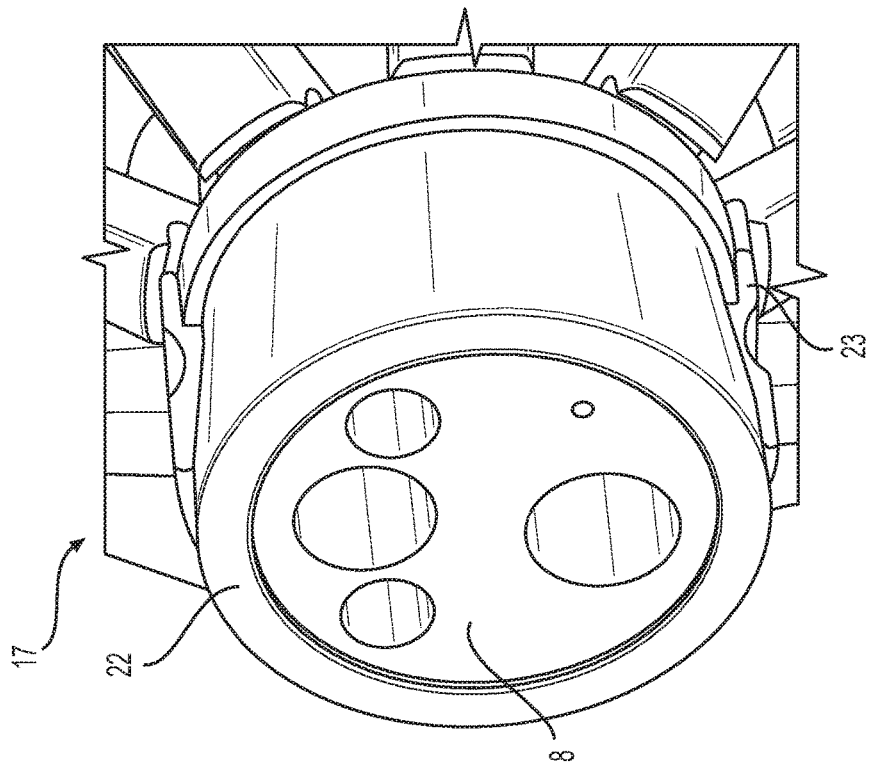
FIG. 17B illustrates a partial cross-section view of an exemplary endoscope tip assembly mounted on an endoscope in a resting position, according to an embodiment of the disclosure.
Figure 17A:
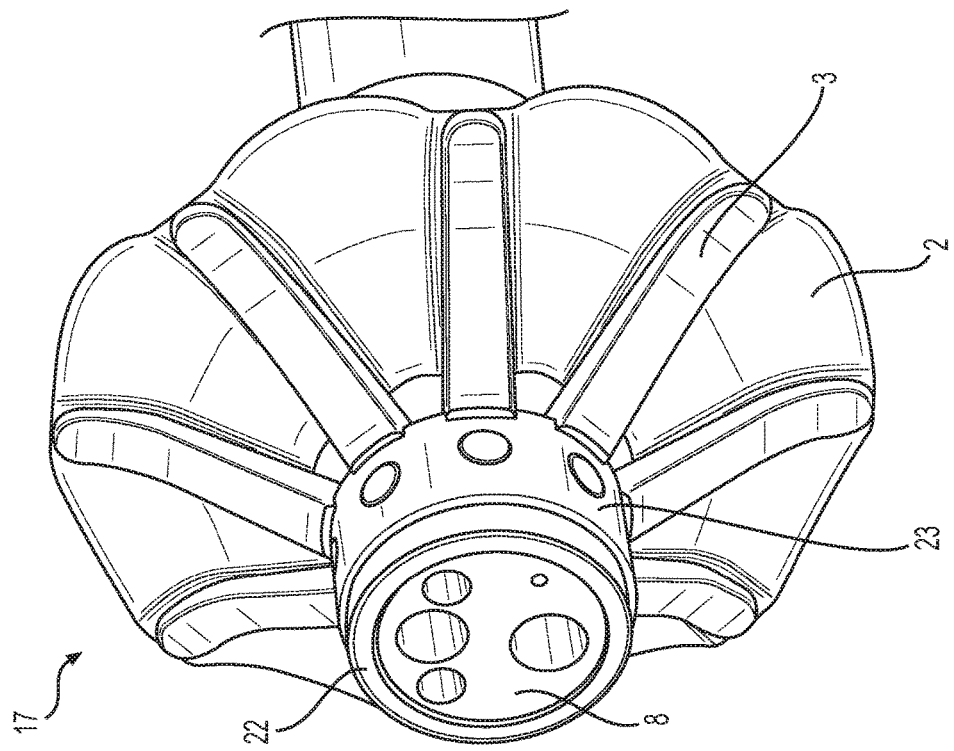
FIG. 17A illustrates an exemplary endoscope tip assembly mounted on an endoscope in a resting position, according to an embodiment of the disclosure.

Reference is now made to FIG. 17B, which illustrates a partial cross-section view of an exemplary endoscope tip assembly mounted on an endoscope in a resting position, according to an embodiment of the disclosure. The cross-section view illustrates the difference in thickness between the proximal and distal ends of sleeve lock 23, and how it makes contact with shaft sleeve 22. In one embodiment, shaft sleeve 22 and sleeve lock 23 may be made out of the same material. In another embodiment, shaft sleeve 22 and sleeve lock 23 may be made out of different materials. The width of sleeve lock 23 may range from about 2 mm to about 10 mm.

Figure 18B:
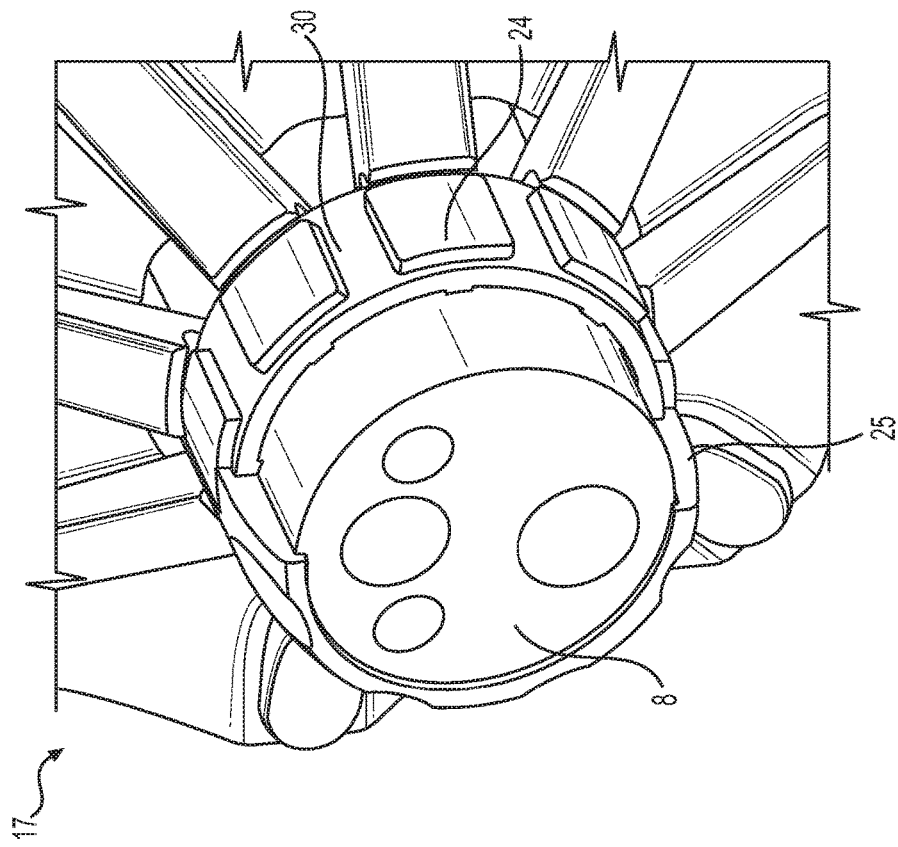
FIG. 18B illustrates a partial cross-section view of an exemplary endoscope tip assembly mounted on an endoscope in a resting position, according to an embodiment of the disclosure.
Figure 18A:
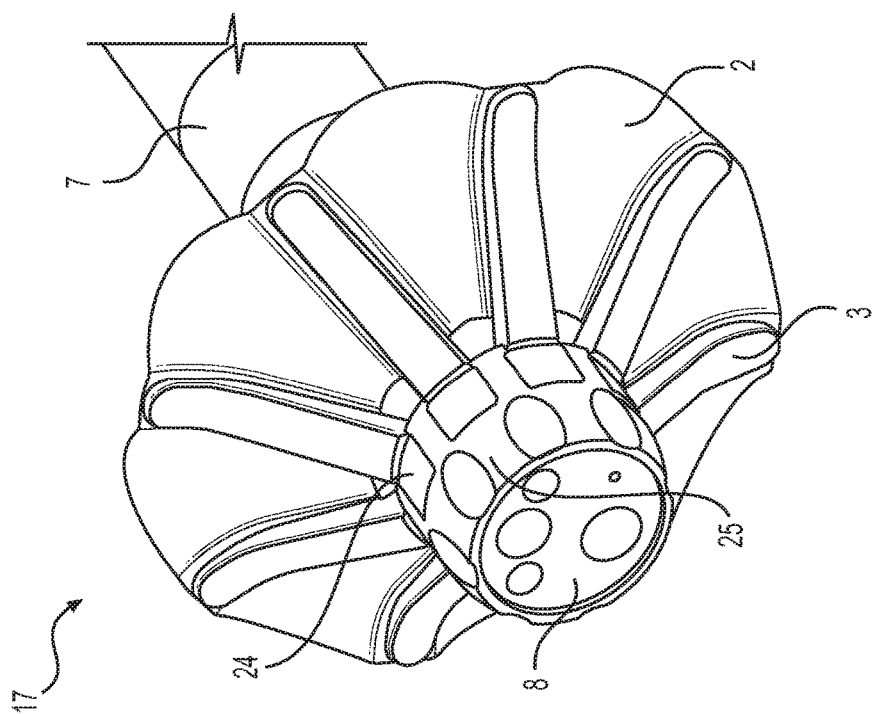
FIG. 18A illustrates an exemplary endoscope tip assembly mounted on an endoscope in a resting position, according to an embodiment of the disclosure.

Reference is now made to FIG. 18A, which illustrates an exemplary endoscope tip assembly mounted on an endoscope in a resting position, according to an embodiment of the disclosure. In one embodiment a plurality of pressure pads 24 may be present. In some embodiments, there may be from about 4 pressure pads 24 to about 12 pressure pads 24. Upon withdrawal, struts 3 may press on and apply pressure to pressure pads 24. As pressure is applied to pressure pads 24, the sliding friction between base 4 and rigid tip 9 of endoscope 10 may increase, and thus may prevent endoscope tip assembly 17 from falling off during a procedure.

Reference is now made to FIG. 18B, which illustrates a partial cross-section view of an exemplary endoscope tip assembly mounted on an endoscope in a resting position, according to an embodiment of the invention. This cross-section view illustrates the contact between sleeve lock 25, pressure pad 24, and shaft sleeve 30. As previously mentioned, during withdrawal, struts 3 may press against and apply pressure to pressure pads 24, which may in turn increase pressure between shaft sleeve 30 and rigid tip 9 of endoscope 10. In one embodiment, shaft sleeve 30 and sleeve lock 25 may be separate pieces. In another embodiment, shaft sleeve 30 and sleeve lock 25 may be one piece. In one embodiment the length of each pressure pad 24 may range from about 2 mm to about 7 mm. In another embodiment, the width of each pressure pad 24 may range from about 2 mm to about 5 mm. In one embodiment, shaft sleeve 30 and sleeve lock 25 may be made from the same material. In another embodiment, shaft sleeve 30 and sleeve lock 25 may be made of different materials. Reference is now made to FIG. 19A, which illustrates a partially exploded view of an exemplary endoscope tip assembly in a resting position, according to an embodiment of the disclosure. In one embodiment, base 4 may contain shaft sleeve 27, sleeve lock 26, and strut support ring 28. These three pieces may work cooperatively to increase sliding friction between shaft sleeve 27 and rigid tip 9 of endoscope 10 to prevent endoscope tip assembly 17 from falling off during a procedure, and/or to provide a rigid surface upon which struts 3 may push during withdrawal. This arrangement may provide for a disengagement force that is greater than the force required to friction fit endoscope tip assembly 17 onto an endoscope tip. In one embodiment, the coefficient of friction between sleeve lock 26 and shaft sleeve 27 may be less than the coefficient of friction between shaft sleeve 27 and rigid tip 9. Sleeve lock 26 may include ribs 11, which may serve to apply additional pressure on shaft sleeve 27, thereby increasing sliding friction between shaft sleeve 27 and rigid tip 9 of endoscope 10. In one embodiment, shaft sleeve 27, sleeve lock 26, and strut support ring 28 may be made of the same material. In another embodiment, shaft sleeve 27, sleeve lock 26, and strut support ring 28 may be made of different materials. Crush ribs 11 have properties as previously discussed.

The inner diameter of sleeve lock 26 is tapered, increasing toward the proximal end, and the taper angle may range from about 0.5° to about 2.5°. The outer diameter of shaft sleeve 27 is also tapered in the same direction, with a diameter of the distal end that is smaller than the diameter of the proximal end. The taper angle of shaft sleeve 27 may vary from about 0.5° to about 2.5°. In one embodiment, the inner diameter of the distal end of sleeve lock 26 may be identical to the outer diameter of the distal end of shaft sleeve 27. In another embodiment, the inner diameter of the distal end of sleeve lock 26 may be slightly less than the outer diameter of the distal end of shaft sleeve 27. For example, in one embodiment, the inner diameter of sleeve lock 26 may be from about 14 mm to about 16 mm for an adult colonoscope. In another embodiment, the outer diameter of shaft sleeve 27 may be from about 14 mm to about 15.5 mm. In one embodiment, the width of sleeve lock 26 may be about the same as the width of shaft sleeve 27. In another embodiment, the width of sleeve lock 26 may be different from that of shaft sleeve 27. In one embodiment, the width of sleeve lock 26 may be from about 5 mm to about 10 mm. In another embodiment, sleeve lock 26 may have a thickness ranging from about 0.4 mm to about 1.5 mm. In another embodiment, shaft sleeve 27 may have a thickness from about 0.3 mm to about 0.75 mm. In one embodiment, strut support ring 28 may have a thickness ranging from about 0.3 mm to about 1.0 mm.

Figure 20B:
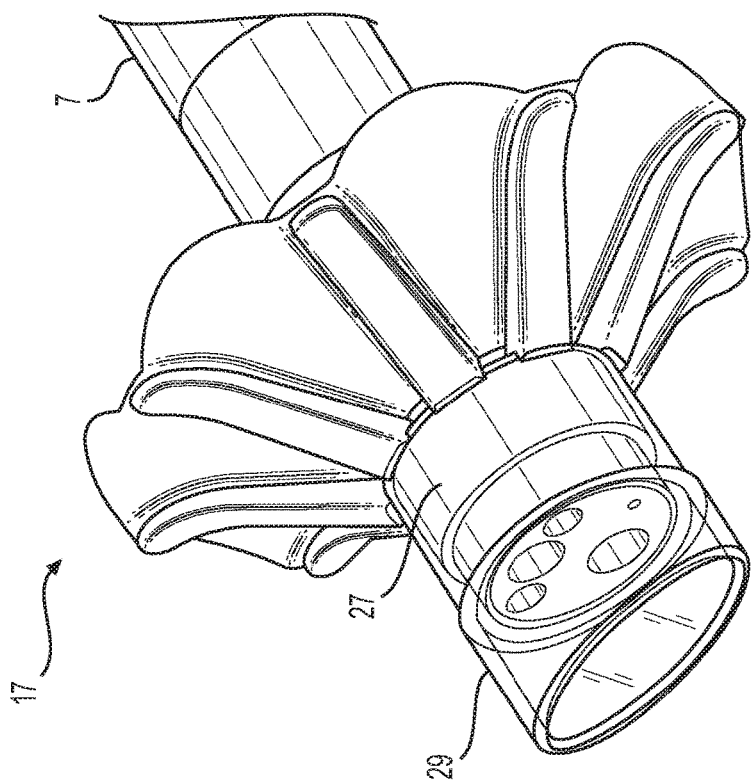
FIG. 20B illustrates an exemplary endoscope tip assembly in a resting position, according to an embodiment of the disclosure.
Figure 20A:
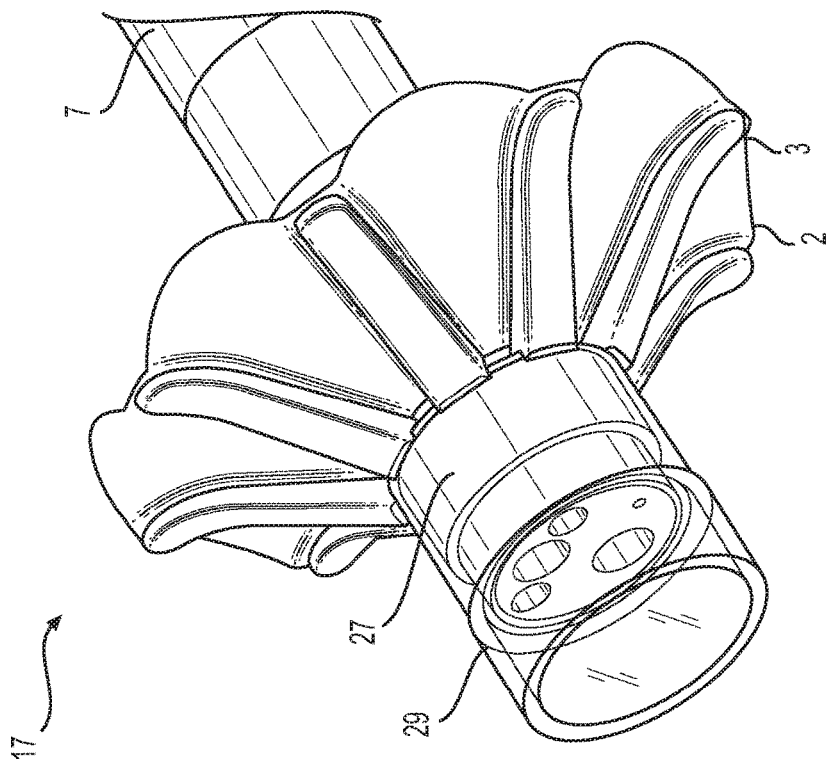
FIG. 20A illustrates an exemplary endoscope tip assembly in a resting position, according to an embodiment of the disclosure.

Reference is now made to FIGS. 20A and 20B, which illustrate an exemplary endoscope tip assembly in a resting position, according to an embodiment of the disclosure. In one embodiment, base 4 may contain distal cap 29 and shaft sleeve 27. These two pieces may work cooperatively to increase sliding friction between shaft sleeve 27 and rigid tip 9 of endoscope 10 to prevent endoscope tip assembly 17 from falling off during a procedure, and/or to provide a rigid surface upon which struts 3 may push during withdrawal. Further, in extending past the end of endoscope 10, distal cap 29 may aid in holding back the lumen such that camera 8 has an unobstructed view. The inner diameter of distal cap 29 may be about the same as the outer diameter of shaft sleeve 27. In another embodiment, the inner diameter of distal cap 29 may be different than the outer diameter of shaft sleeve 27. In one embodiment, the inner diameter of distal cap 29 may range from about 12 mm to about 17 mm. In another embodiment, the outer diameter of shaft sleeve 27 may be from about 13 mm to about 15 mm. In one embodiment, such as, for example, FIG. 20A, the width of distal cap 29 may be consistent along the circumference and may range from about 2 mm to about 8 mm. In another embodiment, such as, for example, FIG. 20B, the width of the distal cap may vary. In some embodiments, the width of distal cap 29 may vary along the circumference of the cap, where the width may range from about 2 mm to about 12 mm.

Figure 21C:
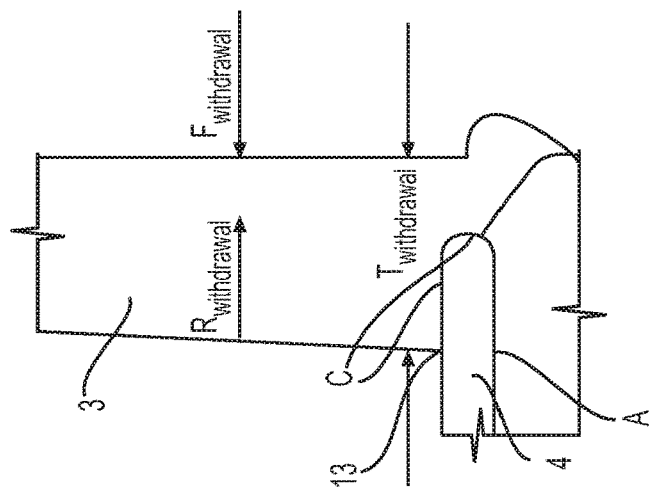
FIG. 21C illustrates a cross-section view of a strut in a withdrawal position, according to an embodiment of the disclosure.
Figure 21B:
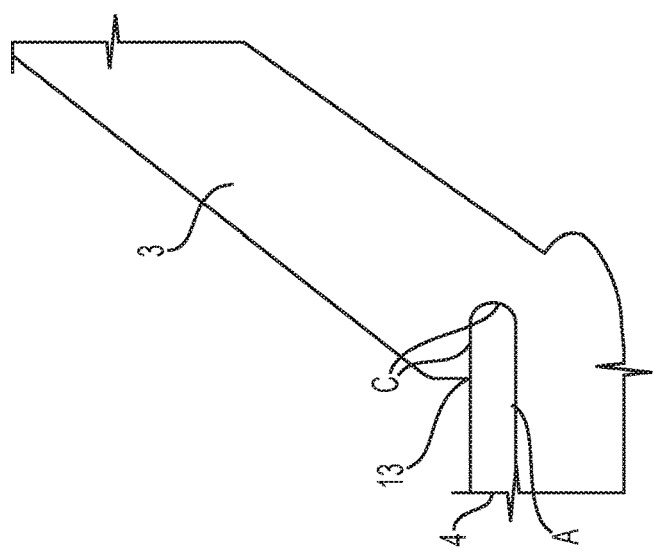
FIG. 21B illustrates a cross-section view of a strut in a resting position, according to an embodiment of the disclosure.
Figure 21A:
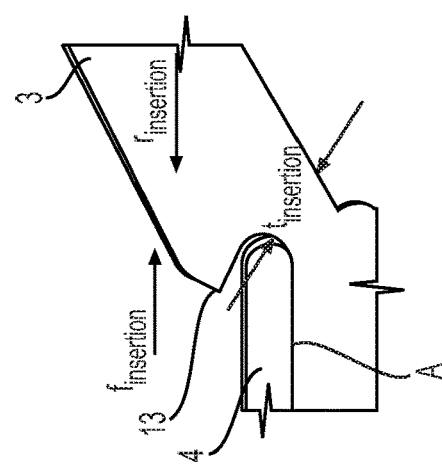
FIG. 21A illustrates a cross-section view of a strut in an insertion position, according to an embodiment of the disclosure.

Reference is now made to FIG. 21A, which illustrates a cross-section view of a strut in an insertion position, according to an embodiment of the disclosure. Base 4 is permanently adhered to strut 3, as indicated by A, however it is not permanently adhered strut 3 at C. During insertion, the insertion force, $f_{insertion}$, needed to flex struts 3 in a proximal direction may be low compared to the force required during withdrawal, $F_{withdrawal}$, because the resistance, $r_{insertion}$, attempting to maintain struts 3 in a resting position, is a cubic function of the thickness of strut 3, $t_{insertion}$, and this thickness may range from about 30% to about 60% of the thickness of strut 3 during withdrawal, $T_{withdrawal}$. Further, as endoscope tip assembly 17 is inserted, no contact is made at C between positive stop 13 and base 4.

Reference is now made to FIG. 21B, which illustrates a cross-section view of a strut in a resting position, according to an embodiment of the disclosure. In a resting position, a contact C exists between base 4 and positive stop 13 of strut 3.

Reference is now made to FIG. 21C, which illustrates a cross-section view of a strut in a withdrawal position, according to an embodiment of the disclosure. Upon withdrawal, contact exists at C, between base 4 and positive stop 13 of strut 3. Further, the resistance to flexing during withdrawal, $R_{withdrawal}$, is a cubic function of the total strut thickness during withdrawal, $T_{withdrawal}$, which may be much greater than the resistance at insertion, $r_{insertion}$. This withdrawal resistance, $R_{withdrawal}$, may assist in maintaining the inverted umbrella-like shape of struts 3 and webbing 2 upon withdrawal.

Figure 22:
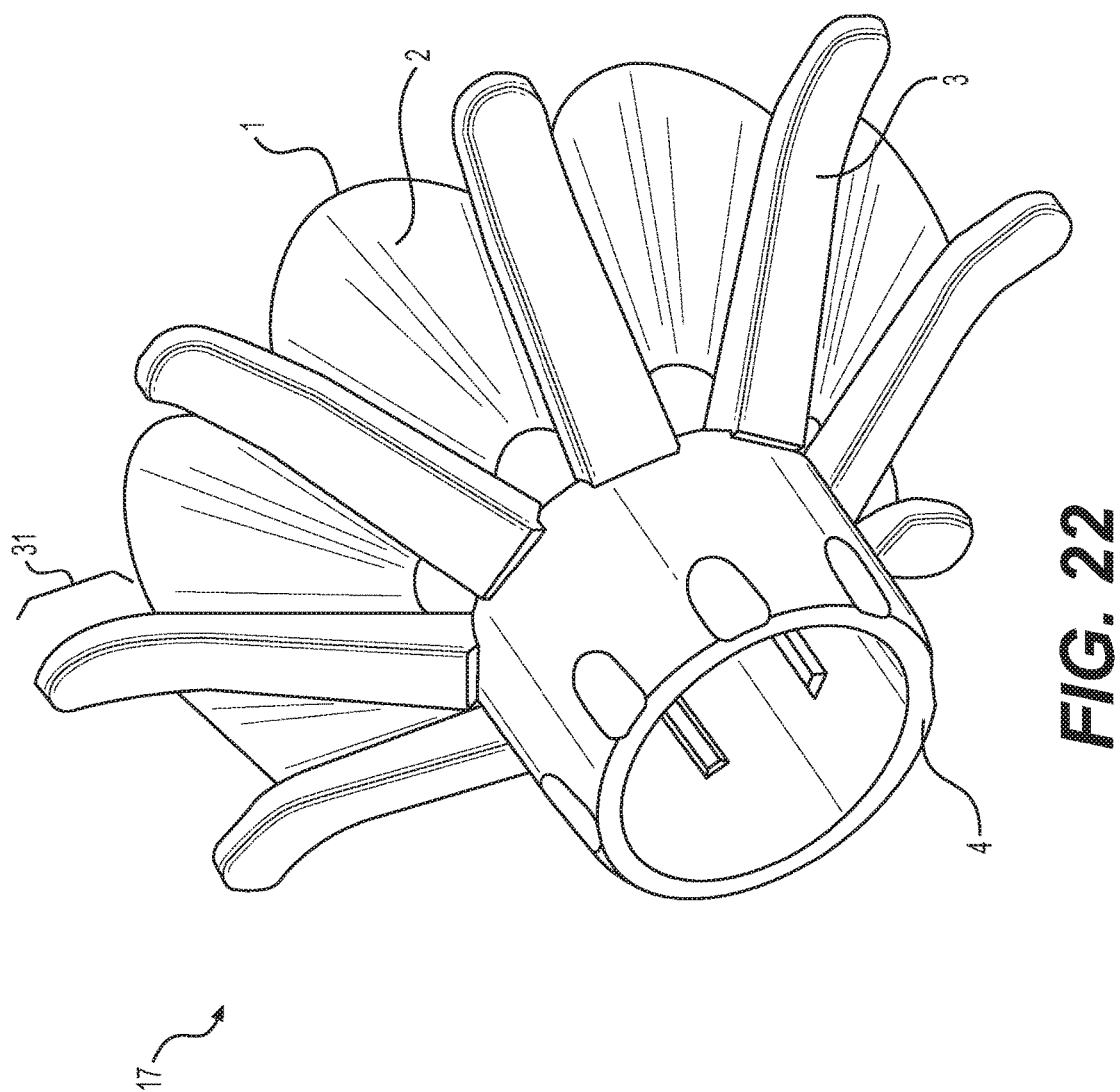
FIG. 22 illustrates an exemplary endoscope tip assembly, with pleated webbing that does not extend to the end of the strut, according to an embodiment of the present disclosure.

Reference is now made to FIG. 22, which illustrates an exemplary endoscope tip assembly, with pleated webbing that does not extend to the end of the strut, according to an embodiment of the present disclosure. Length 31 represents the distance between the tip of strut 3 and the edge of webbing 2. In some embodiments, length 31 may be 0 mm, as illustrated in FIG. 1. In some embodiments, length 31 may range from about 0 mm to about 15 mm. In other embodiments, length 31 may range from about 3 mm to about 10 mm. This length 31, when greater than 0 mm, may facilitate better visualization of the inside of the colon during the procedure, as there may be less webbing 2 to obstruct the camera's view.

Figure 23:
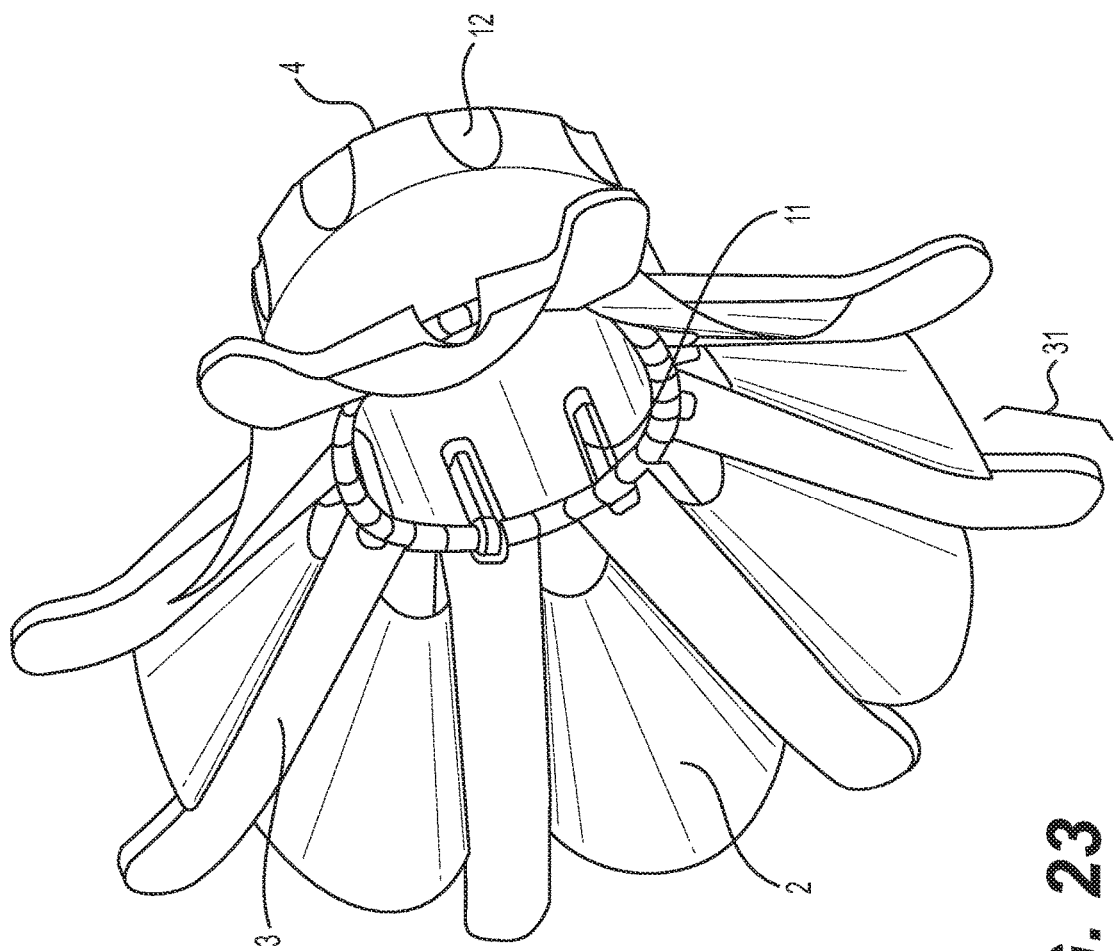
FIG. 23 illustrates an exemplary endoscope tip assembly, with pleated webbing that does not extend to the end of the strut, according to an embodiment of the present disclosure.

Reference is now made to FIG. 23, which illustrates an exemplary endoscope tip assembly, with pleated webbing that does not extend to the end of the strut, according to an embodiment of the present disclosure. FIG. 23 provides an alternative view of the embodiment illustrated in FIG. 22, where length 31 is a non-zero distance.

Figure 24:
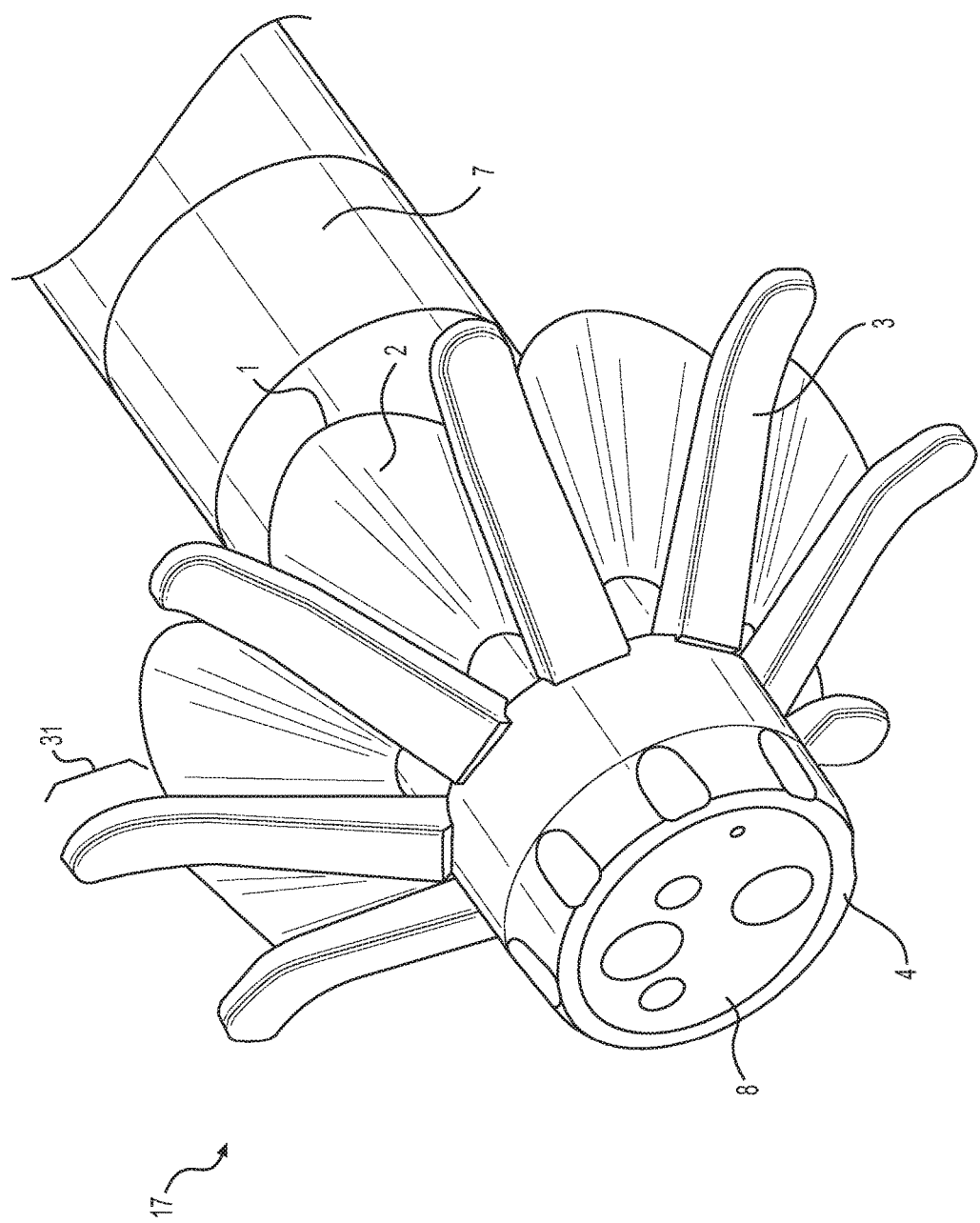
FIG. 24 illustrates an exemplary endoscope tip assembly mounted on an endoscope in a resting position, according to an embodiment of the disclosure.

Reference is now made to FIG. 24, which illustrates an exemplary endoscope tip assembly mounted on an endoscope in a resting position, according to an embodiment of the disclosure. Length 31 may be 0 mm, as illustrated in FIG. 6, or, in some embodiments, length 31 may range from about 0 mm to about 15 mm, as illustrated in, for example, FIG. 24. In some embodiments, the radial length of webbing 2 may range from about 25% to about 100% of the length of the strut.

Figure 25A:
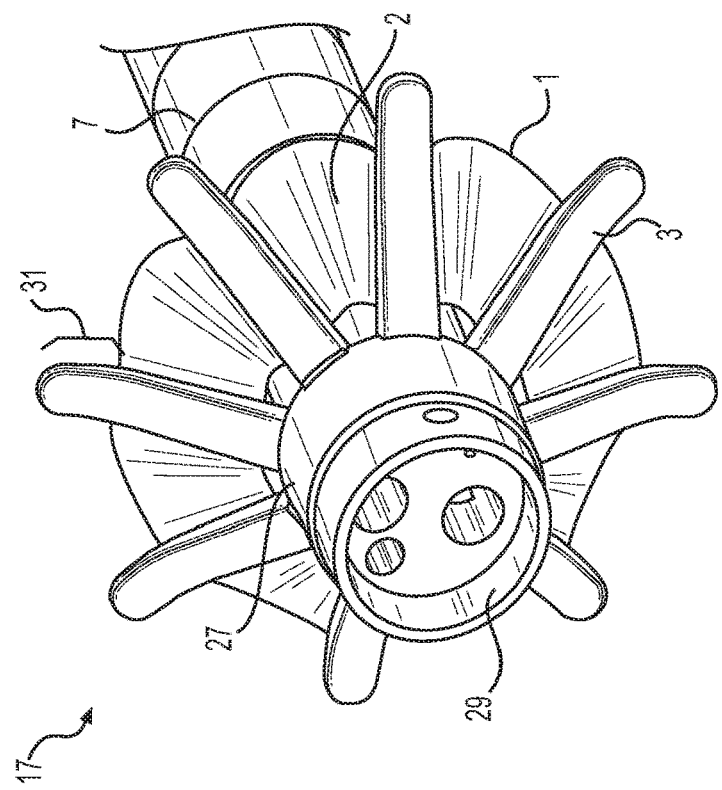
FIG. 25A illustrates an exemplary endoscope tip assembly mounted on an endoscope in a resting position, according to an embodiment of the disclosure.
Figure 25B:
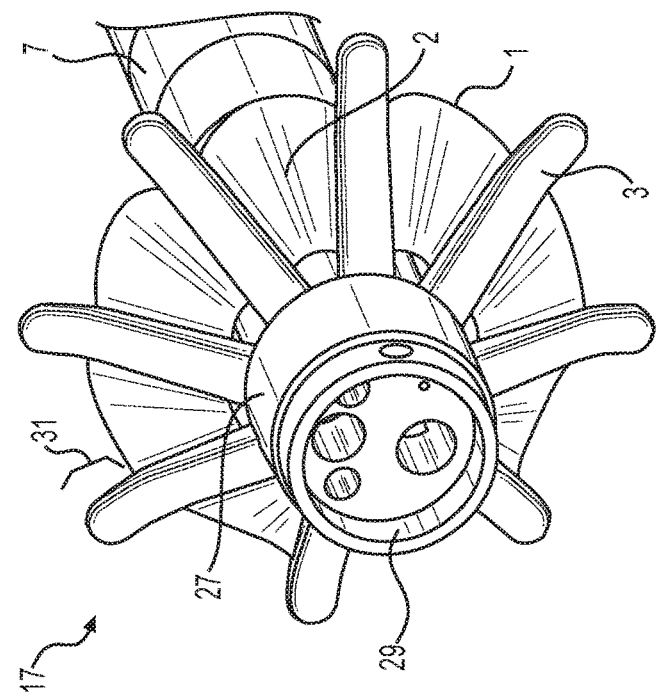
FIG. 25B illustrates an exemplary endoscope tip assembly mounted on an endoscope in a resting position, according to an embodiment of the disclosure.

Reference is now made to FIG. 25A, which illustrates an exemplary endoscope tip assembly mounted on an endoscope in a resting position, according to an embodiment of the disclosure. Length 31 may be 0 mm, as illustrated in, for example, FIG. 6, or, in some embodiments, length 31 may range from about 0 mm to about 15 mm, as illustrated in, for example, FIG. 24. In one embodiment, base 4 may contain distal cap 29 and shaft sleeve 27. These two pieces may work cooperatively to aid in holding back the lumen such that camera 8 has an unobstructed view. In one embodiment, such as, for example, FIG. 25A, the width of the distal cap may be consistent along the circumference and may range from about 2 mm to about 8 mm. In another embodiment, such as, for example, FIG. 25B, the width of the distal cap 29 may vary along the circumference of the cap, where the width may range from about 2 mm to about 12 mm.

In some embodiments, a method for improved visualization during endoscopic procedures is provided, wherein an endoscope tip assembly of the present disclosure is mounted on the distal end of an endoscope prior to the procedure.

In some embodiments, a method for improved endoscope stabilization during endoscopic procedures is provided, wherein an endoscope tip assembly of the present disclosure is mounted on the distal end of an endoscope prior to the procedure.

In some embodiments, a method for less traumatic endoscopic procedures is provided, wherein an endoscope tip assembly of the present disclosure is mounted on the distal end of an endoscope prior to the procedure.

While the present disclosure is described herein with reference to illustrative embodiments of endoscope attachments used for particular applications, such as for performing medical procedures, it should be understood that the embodiments described herein are not limited thereto. For example, scopes and similar devices are often used in industrial applications, e.g., to inspect and/or repair machinery. Endoscope attachments of the present disclosure may also be used with industrial scopes in non-medical settings. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. An endoscope tip assembly, comprising:
a ring-shaped base having a substantially cylindrical inner surface that is dimensioned to receive a distal end of an endoscope; and
a collapsible umbrella extending radially out from the base, wherein the collapsible umbrella includes:
a webbing forming a collapsible surface; and
a plurality of flexible struts extending along the webbing and configured to flex to transition the collapsible umbrella between an insertion state and a withdrawal state;
wherein each of the plurality of struts is attached to the inner surface of the base and extend from the inner surface, around an edge of the base, and radiate away from an outer surface of the base terminating at a tip;
wherein the webbing is continuous and is connected to each of the plurality of struts; and
wherein, in the insertion state, the plurality of struts are flexed toward a direction extending substantially parallel with the outer surface of the base and the tip of each of the plurality of struts is pointed in a proximal direction, and wherein, in the withdrawal state, the plurality of struts are flexed outward away from the outer surface of the base and the tip of each of the plurality of struts is pointed in a distal direction substantially parallel to the outer surface of the base.

2. The endoscope tip assembly of claim 1, wherein a force required to flex the plurality of struts to transition the collapsible umbrella to the insertion state is less than a force required to flex the plurality of struts to transition the collapsible umbrella to the withdrawal state.

3. The endoscope tip assembly of claim 1, wherein the tip of each of the plurality of struts is off-axis from an intermediate portion of each of the plurality of struts.

4. The endoscope tip assembly of claim 1, wherein at least one of the plurality of struts includes one or more notches located along a distal-facing surface of the strut.

5. The endoscope tip assembly of claim 1, wherein the base is substantially rigid.

6. The endoscope tip assembly of claim 1, wherein the inner surface of the base includes at least one crush rib projecting from the inner surface.

7. The endoscope tip assembly of claim 1, wherein the webbing is pleated.

8. The endoscope tip assembly of claim 1, wherein the outer surface of the base includes at least one gripping structure.

9. The endoscope tip assembly of claim 1, wherein the outer surface of the base includes at least one self-locking window.

10. The endoscope tip assembly of claim 1, wherein the base further comprises:
a shaft sleeve;
a sleeve lock; and
a strut support ring.

11. The endoscope tip assembly of claim 1, wherein the base further comprises:
a distal cap; and
a shaft sleeve.

* * * * *